US009140701B2

(12) United States Patent
Robinson et al.

(10) Patent No.: US 9,140,701 B2
(45) Date of Patent: Sep. 22, 2015

(54) FIBRINOGEN IMMUNE COMPLEXES TO DIAGNOSE AND GUIDE THERAPY IN RHEUMATOID ARTHRITIS

(75) Inventors: William H. Robinson, Palo Alto, CA (US); Peggy Pui-Kay Ho, Cupertino, CA (US); Xiaoyan Zhao, Stanford, CA (US); Lawrence M. Steinman, Stanford, CA (US)

(73) Assignee: THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 502 days.

(21) Appl. No.: 12/806,081

(22) Filed: Aug. 4, 2010

(65) Prior Publication Data

US 2011/0047632 A1    Feb. 24, 2011

Related U.S. Application Data

(60) Provisional application No. 61/274,634, filed on Aug. 18, 2009.

(51) Int. Cl.
| | |
|---|---|
| *G01N 33/53* | (2006.01) |
| *G01N 33/566* | (2006.01) |
| *G01N 33/564* | (2006.01) |
| *G01N 33/50* | (2006.01) |

(52) U.S. Cl.
CPC .......... *G01N 33/564* (2013.01); *G01N 33/5082* (2013.01); *G01N 2333/75* (2013.01); *G01N 2500/00* (2013.01); *G01N 2800/102* (2013.01); *G01N 2800/52* (2013.01); *G01N 2800/56* (2013.01)

(58) Field of Classification Search
CPC .................... G01N 2800/102; G01N 2800/52; G01N 2800/56
See application file for complete search history.

(56) References Cited

U.S. PATENT DOCUMENTS

| | | | | |
|---|---|---|---|---|
| 7,445,903 | B2 * | 11/2008 | Serre et al. .................... | 435/7.1 |
| 2003/0003516 | A1 * | 1/2003 | Robinson et al. ............. | 435/7.9 |
| 2007/0009507 | A1 * | 1/2007 | Serre et al. ................. | 424/131.1 |
| 2008/0096233 | A1 * | 4/2008 | Robotti et al. ............... | 435/7.23 |
| 2008/0318872 | A1 * | 12/2008 | Xu ................................. | 514/19 |
| 2009/0142792 | A1 * | 6/2009 | Robinson et al. ............. | 435/29 |

OTHER PUBLICATIONS

Melsom et al., (Rheumatol Int. 1986;6(5):227-31; abstract only).*
Zhao et al., (Arth Res Ther. Aug. 18, 2008;10(4):R94(13 pages) (cited on Applicant's IDS of Nov. 18, 2010.*
Hill; et al., "Arthritis induced by posttranslationally modified (citrullinated) fibrinogen in DR4-IE transgenic mice", The Journal of Experimental Medicine (2008), 205(4):967-979.
Hueber; et al., "Antigen Microarray Profiling of Autoantibodies in Rheumatoid Arthritis", Arthritis & Rheumatism (2005), 52(9):2645-2655.

(Continued)

*Primary Examiner* — Cherie M Stanfield
(74) *Attorney, Agent, or Firm* — Bozicevic, Field & Francis LLP; Pamela J. Sherwood

(57) ABSTRACT

Compositions and methods are provided for prognostic classification of rheumatoid arthritis disease patients into subtypes, which subtypes are informative of the patient's need for therapy and responsiveness to a therapy of interest.

4 Claims, 28 Drawing Sheets
(16 of 28 Drawing Sheet(s) Filed in Color)

(56) References Cited

OTHER PUBLICATIONS

Hueber; et al., "Proteomic analysis of secreted proteins in early rheumatoid arthritis: anti-citrulline autoreactivity is associated with up regulation of proinflammatory cytokines", Ann Rheum Dis (2007), 66:712-719.

Kidd; et al., "Epitope spreading to citrullinated antigens in mouse models of autoimmune arthritis and demyelination", Arthritis Research & Therapy (2008), 10(5):R119, 12 pages.

Zhao; et al., "Circulating immune complexes contain citrullinated fibrinogen in rheumatoid arthritis", Arthritis Research & Therapy (2008), 10(4):R94, 13 pages.

* cited by examiner

Fibrinogen immune complex correlates with disease severity

H2B containing immune complexes are elevated in anti-CCP+ RA plasma

Fibronectin containing immune complexes in RA synovial fluid

FIBRINOGEN IMMUNE COMPLEXES TO DIAGNOSE AND GUIDE THERAPY IN RHEUMATOID ARTHRITIS

CROSS REFERENCE TO RELATED APPLICATIONS

Pursuant to 35 U.S.C. §119(e), this application claims priority to the filing date of the U.S. Provisional Patent Application Ser. No. 61/274,634 filed Aug. 18, 2009; the disclosure of which is herein incorporated by reference.

FEDERALLY SPONSORED RESEARCH AND DEVELOPMENT

This invention was made with Government support under grant R21-AI-069160 awarded by the National Institutes of Health. The Government has certain rights in this invention.

BACKGROUND OF THE INVENTION

Rheumatoid arthritis (RA), a chronic inflammatory disease of the synovial joints, afflicts up to 1.0% of the adult population worldwide, yet our understanding of the etiology and pathogenesis of RA remains limited. In RA, synovial inflammation results in growth of the synovial lining to form pannus tissue, which contributes to cartilage and joint destruction.

Although RA involves autoimmune reactions, the precise cause is unknown; and many factors may contribute. A genetic predisposition has been identified and, in white populations, localized to a shared epitope in the HLA-DR $\beta_1$ locus of class II histocompatibility antigens. Unknown environmental factors, e.g., viral infections, smoking, etc. are also thought to play a role. RA is characterized by the production of, autoantibodies, including rheumatoid factor (RF; IgM antibody against the Fc portion of IgG) and anti-citrullinated protein antibodies (ACPAs) that have binding specificity for citrulline-containing proteins such as perinuclear factor, vimentin, filaggrin and fibrinogen. Prominent immunologic abnormalities include immune complexes produced by synovial lining cells and in inflamed blood vessels. Macrophages also migrate to diseased synovium in early disease; increased macrophage-derived lining cells are prominent along with vessel inflammation.

In chronically affected joints, the normally thin synovium thickens and develops many villous folds. The synovial lining cells produce various materials, including collagenase and stromelysin, which contribute to cartilage destruction, and IL-1 and TNF-α, which stimulate cartilage destruction, osteoclast-mediated bone absorption, synovial inflammation, and prostaglandins. Fibrin deposition, fibrosis, and necrosis are also present.

Rheumatoid factors (RF), antibodies to human γ-globulin, are present in about 70% of patients with RA. However, RF, often in low titers, occurs in patients with other diseases, including other connective tissue diseases such as systemic lupus erythematosus, granulomatous diseases, chronic infections such as viral hepatitis, subacute bacterial endocarditis, and tuberculosis, and cancers. Low RF titers can also occur in a small percentage of the general population, and more commonly in the elderly.

Another disease indicator is the presence of anti-CCP (cyclic citrullinated peptide) antibodies, which have a high specificity and sensitivity for RA and, like RF, predict a worse prognosis.

Diagnostic methods for predicting the severity of rheumatoid arthritis are of great clinical interest. The present invention addresses this issue.

Publications

Autoantibody profiles and uses thereof are described in U.S. Patent application, publication US-2003-0003516-A1, herein incorporated by reference.

Epitope spreading to citrullinated antigens in mouse models of autoimmune arthritis and demyelination is described by Kidd et al. (2008) Arthritis Res Ther. 10(5):R119. Zhao et al. (2008) Arthritis Res Ther. 10(4):R94 describe immune complexes contain citrullinated fibrinogen. Arthritis induced by posttranslationally modified (citrullinated) fibrinogen in DR4-IE transgenic mice is described by Hill et al. (2008) J Exp Med. 205(4):967-79. Proteomic analysis of secreted proteins in early rheumatoid arthritis is described by Hueber et al. (2007) Ann Rheum Dis. 66(6):712-9. Antigen microarray profiling of autoantibodies in rheumatoid arthritis is described by Hueber et al. (2005) Arthritis Rheum. 52(9): 2645-55.

SUMMARY OF THE INVENTION

Methods are provided for prognostic classification of individuals with respect to severity of rheumatoid arthritis, including, without limitation, juvenile rheumatoid arthritis patients. The methods of the invention comprise the steps of: detecting circulating immune complexes comprising citrullinated fibrinogen (ICCF) in a sample obtained from the individual; analyzing the ICCF content relative to a normal control; and providing an assessment of prognosis, where the presence of the ICCF is indicative of a more severe disease prognosis. Where the individual is a juvenile, the presence of ICCF is indicative of a phenotype usually associated with adult RA. In some embodiments, the prognosis is used to guide decisions of patient care, thus allowing improved therapeutic choices. Prognosis may also include clinical, imaging, laboratory and genetic parameters to assess an individual patient's disease state and thereby determine if they would benefit from initiation of therapy.

In some embodiments, the detection of ICCF is performed by obtaining patient sample, which may be blood, a blood derivative such as plasma, etc.; and in an immunoassay format, e.g. ELISA, RIA, contacting the sample with a reagent that selectively binds to immune complexes. Reagents of interest for this purpose include, without limitation, C1q protein and anti-C1q antibody. The presence of citrullinated fibrinogen in the complexes may be determined with a second antibody specific for fibrinogen.

In another embodiment of the invention, animal models are provided for rheumatoid arthritis. The models are useful for testing and screening of biologically active agents for the treatment of inflammatory joint disease. A rodent, e.g. a mouse, having a functional immune system, is immunized with the native form of fibrinogen. The resulting fibrinogen induced arthritis (FIA) provides robust T-cell reactivity to native fibrinogen and B-cell reactivity to native fibrinogen, citrullinated fibrinogen, and other candidate RA autoantigens. Disease can be transferred with either fibrinogen-reactive T cells or plasma from FIA mice. Mice with FIA possess RF, anti-CCP antibodies, and IgG immune complexes, all of which are characteristic of a subset of human RA patients. Compared to the arthritis that develops in other murine models of RA, FIA is mild to moderate and therefore more closely resembles human RA. Another advantage of the FIA model is that it does not rely on genetically altered mice expressing a TCR-encoding transgene or mutated form of CD45, but rather uses wild-type mice, e.g. SJL or DBA/1 which are common mouse strains that are readily available.

A cell population comprising immunocompetent effector cells, which lacks $CD25^+$ suppressor T cells, is transferred into a cellular environment that lacks $CD25^+$ suppressor T cells but contains a T cell antigen. Preferably, an immunostimulant and/or immunomodulatory co-factor and/or T cell antigen is introduced at a targeted site or organ after the T cell introduction to enhance T cell response and homing. Animals develop acute and chronic inflammatory responses at the targeted site, and provide a useful model for the development of inflammation, and for drug/gene screening in the prevention and treatment of chronic inflammatory disease in humans.

In other embodiments of the invention a device or kit is provided for the analysis of patient samples. Such devices or kits will include reagents that selectively identify fibrinogen immune complexes. Devices of interest include arrays, where the reagents are spatially separated on a substrate such as a slide, gel, multi-well plate, etc. Alternatively the reagents may be provided as a kit comprising reagents in a suspension or suspendable form, e.g. reagents bound to beads suitable for flow cytometry, and the like.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE EMBODIMENTS

Figure 1:
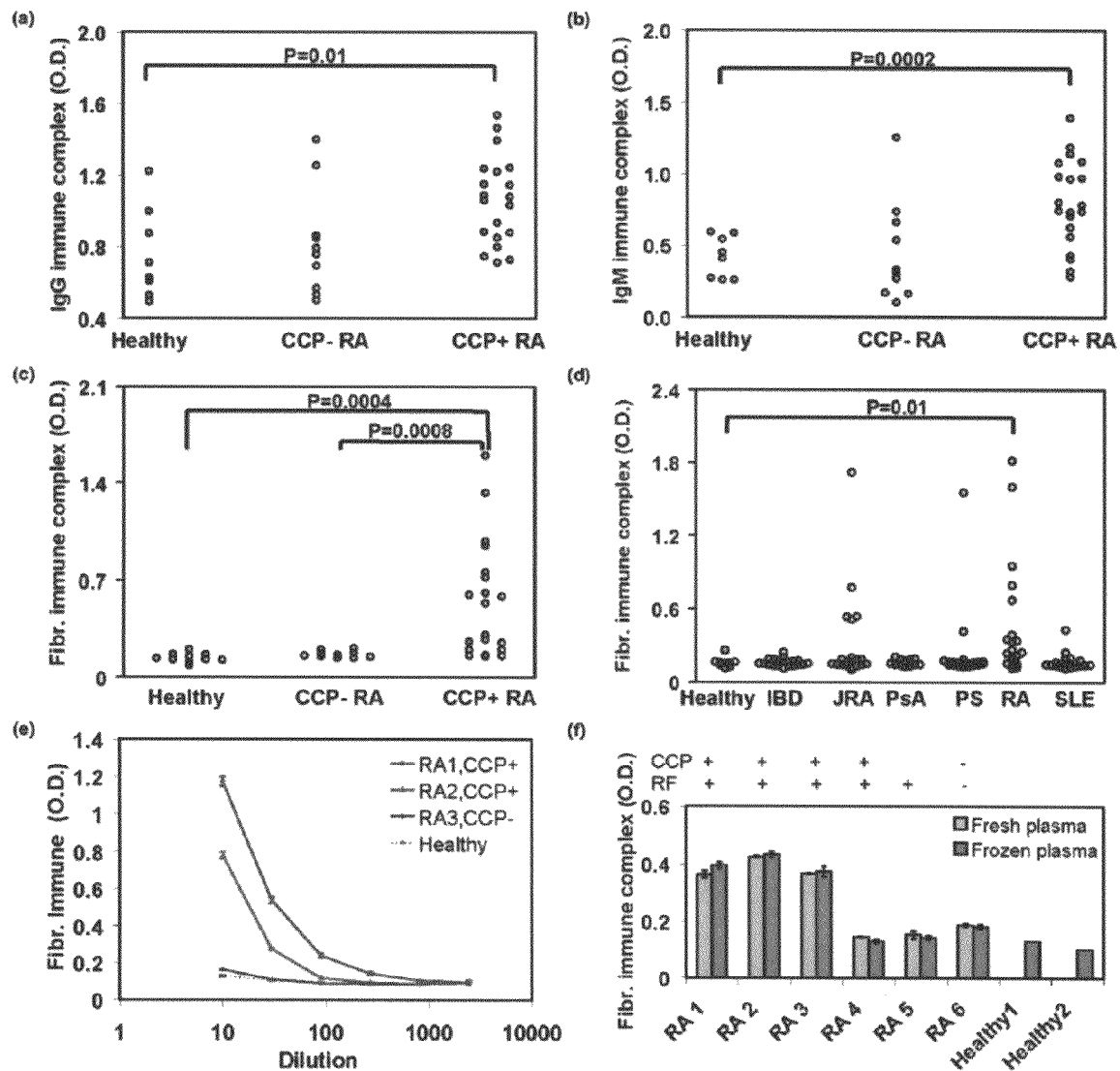
FIG. 1. Fibrinogen-containing circulating immune complexes in RA. A and B, Circulating IgG (A) and IgM (B) ICs were detected in plasma derived from healthy individuals and CCP− and CCP+ RA patients. ELISA plates were coated with C1q, incubated with 1:50 dilutions of plasma samples, and HRP-conjugated anti-IgG (A) or anti-IgM (B) secondary antibodies were used to detect the immunoglobulin isotypes contained in immune complexes. C and D, Circulating fibrinogen-containing ICs were detected using HRP-conjugated fibrinogen-specific antisera as the secondary reagent. Statistical comparisons are based on an unpaired t-test with Welch correction. E, Fibrinogen-containing ICs were detected with different dilutions of RA patient samples and healthy controls. Error bars represent the standard deviation of results from triplicate wells. F, Fibrinogen-containing ICs were detected in fresh plasma and freeze-thawed plasma samples with no significant differences in values.

Compositions and methods are provided for prognostic classification of rheumatoid arthritis patients according to the prognosis for disease severity and long-term clinical outcome. The methods of the invention comprise the steps of: detecting circulating immune complexes comprising citrullinated fibrinogen (ICCF) in a sample obtained from the individual; analyzing the ICCF content relative to a normal control; and providing an assessment of prognosis, where the presence of the ICCF is indicative of a more severe disease prognosis. The prognostic information may be used to guide clinical decision making, both in terms, of institution of and escalation of therapy as well as in the selection of the therapeutic agent to which the patient is most likely to exhibit a robust response.

Definitions

Immune Complexes. Immune complexes are clusters of interlocking antigens and antibodies, which typically comprise at least one antibody and at least one antigen, but which may comprise multiples, e.g. two antibody:antigen complexes, three complexes, or more. In some cases the immune complex further comprises C1q protein. C1q is a subunit of the C1 enzyme complex that activates the serum complement system, and comprises 6 A, 6 B and 6 C chains (see Sellar et al. (1991) Biochem. J. 274 (Pt 2) 481-90).

Under normal conditions immune complexes are rapidly removed from the bloodstream by macrophages in the spleen and Kupffer cells in the liver. In some circumstances, however, immune complexes continue to circulate, and become trapped in tissues, leading to inflammation and tissue damage.

Fibrinogen is a blood-borne glycoprotein comprised of three pairs of nonidentical polypeptide chains. Following vascular injury, fibrinogen is cleaved by thrombin to form fibrin which is the most abundant component of blood clots. The N-terminal sections of these three chains contain the cysteines that participate in the cross-linking of the chains. The C-terminal parts of the α and β chains contain a domain of about 225 amino-acid residues, which can function as a molecular recognition unit. In addition, various cleavage products of fibrinogen and fibrin regulate cell adhesion and spreading, display vasoconstrictor and chemotactic activities, and are mitogens for several cell types. The genetic sequence of human fibrinogen alpha chain may be accessed at Genbank, accession number NM_000508. The genetic sequence of human fibrinogen beta chain may be accessed at Genbank, accession number NM_005141. The genetic sequence of human fibrinogen gamma chain may be accessed at Genbank, accession number NM_000509.

The fibrinogen present in immune complexes of the present invention comprise one or more citrulline residues. The results provided herein are consistent with citrulline being present in the beta-chain of fibrinogen, although residues may also be present in the alpha and gamma chains.

Although citrulline is not coded for by DNA directly, several proteins are known to contain citrulline as a result of a posttranslational modification. These citrulline residues are generated by a family of enzymes called peptidylarginine deiminases (PADs), which convert arginine into citrulline in a process called citrullination or deimination. Proteins that normally contain citrulline residues include myelin basic protein (MBP), filaggrin, keratin, and several histone proteins, whereas other proteins, such as fibrin and vimentin are susceptible to citrullination during cell death and tissue inflammation.

Rheumatoid Arthritis is a chronic syndrome characterized by usually symmetric inflammation of the peripheral joints, potentially resulting in progressive destruction of articular and periarticular structures, with or without generalized manifestations. The cause is unknown. A genetic predisposition has been identified and, in white populations, localized to a pentapeptide in the HLA-DR beta1 locus of class II histocompatibility genes. Environmental factors may also play a role. Immunologic changes may be initiated by multiple factors. About 0.6% of all populations are affected, women two to three times more often than men. Onset may be at any age, most often between 25 and 50 yr.

Prominent immunologic abnormalities that may be important in pathogenesis include immune complexes found in joint fluid cells and in vasculitis. Plasma cells produce antibodies that contribute to these complexes. Lymphocytes that infiltrate the synovial tissue are primarily T helper cells, which can produce pro-inflammatory cytokines. Macrophages and their cytokines (e.g., tumor necrosis factor, granulocyte-macrophage colony-stimulating factor) are also abundant in diseased synovium. Increased adhesion molecules contribute to inflammatory cell emigration and retention in the synovial tissue. Increased macrophage-derived lining cells are prominent along with some lymphocytes and vascular changes in early disease.

In chronically affected joints, the normally delicate synovium develops many villous folds and thickens because of increased numbers and size of synovial lining cells and colonization by lymphocytes and plasma cells. The lining cells produce various materials, including collagenase and stromelysin, which can contribute to cartilage destruction; interleukin-1, which stimulates lymphocyte proliferation; and prostaglandins. The infiltrating cells, initially perivenular but later forming lymphoid follicles with germinal centers, synthesize interleukin-2, other cytokines, RF, and other immunoglobulins. Fibrin deposition, fibrosis, and necrosis also are present. Hyperplastic synovial tissue (pannus) may erode cartilage, subchondral bone, articular capsule, and ligaments. PMNs are not prominent in the synovium but often predominate in the synovial fluid.

Onset is usually insidious, with progressive joint involvement, but may be abrupt, with simultaneous inflammation in multiple joints. Tenderness in nearly all inflamed joints is the most sensitive physical finding. Synovial thickening, the most specific physical finding, eventually occurs in most involved joints. Symmetric involvement of small hand joints (especially proximal interphalangeal and metacarpophalangeal), foot joints (metatarsophalangeal), wrists, elbows, and ankles is typical, but initial manifestations may occur in any joint.

Mammalian species for analysis include canines; felines; equines; bovines; ovines; etc. and primates, particularly humans. Animal models, particularly small mammals, e.g. murine, lagomorpha, etc. may be used for experimental investigations. Animal models of interest include those for models of autoimmunity, graft rejection, and the like.

Sample. Patient samples, as used herein, comprise biological material from a patient suspected of having rheumatoid arthritis. Samples can be obtained from the tissues or fluids of an individual. For example, samples can be obtained from whole blood; tissue biopsy, serum, etc. Other sources of samples are body fluids such as synovial fluid, lymph, cerebrospinal fluid, bronchial aspirates, and may further include saliva, milk, urine, and the like. Also included in the term are derivatives and fractions of such cells and fluids. Diagnostic samples are collected any time after an individual is suspected to have an autoimmune disease or has exhibited symptoms that predict such a disease. Optionally the sample is treated to block or deplete heterophilic antibodies, e.g. RF. The ICCF of the invention are found in patient circulation, and so preferred samples are blood samples, or samples derived from blood, e.g. plasma, serum, etc.

Juvenile rheumatoid arthritis (JRA). JRA is a group of rheumatic diseases that begins at or before age 16. Arthritis, fever, rash, adenopathy, splenomegaly, and iridocyclitis are typical of some forms. Diagnosis is clinical. Treatment involves NSAIDs and disease-modifying antirheumatic drugs.

Patients with JIA can have joint stiffness, swelling, effusion, pain, and tenderness. JIA may interfere with growth and development. Micrognathia (receded chin) due to early closure of mandibular epiphyses may occur. Iridocyclitis may develop, which may cause conjunctival injection, pain, and photophobia but can be asymptomatic; scarring and glaucoma with band keratopathy can result. The initial symptoms and signs of JIA tend to fall into 3 possible patterns.

Systemic onset (Still's disease) occurs in about 20% of patients. High fever, rash, splenomegaly, generalized adenopathy, and serositis with pericarditis or pleuritis are common. These may precede the development of arthritis. A typical transient rash often appears with the fever or may be diffuse and migratory, with urticarial or macular lesions.

Pauciarticular onset is characterized by involvement of ≥4 joints. It occurs in about 40% of patients, usually young girls. Iridocyclitis is most common in pauciarticular JIA, developing in nearly 20%. Many affected older boys have the HLA-B27 allele.

Polyarticular onset involves ≥5 joints, often ≥20. It occurs in the remaining 40% of patients and is often similar to adult RA. Arthritis tends to be symmetric and develop slowly.

Patients suspected of having JRA are generally tested for RF, ANA, and ESR because these tests may be helpful in distinguishing its subtypes. In Still's disease, RF and ANA are absent. In pauciarticular-onset, ANA are present in up to 75% and RF is absent. In polyarticular-onset, RF may be positive.

Complete remissions occur in 50 to 75% of treated patients. Patients with polyarticular onset and a positive RF have a less favorable prognosis. Conventional treatment is NSAIDs, although disease-modifying antirheumatic drugs (DMARDs), particularly the biologic agents, may also be used.

Therapy. Classes of drugs commonly used in the non-antigen specific treatment of RA include corticosteroids and disease modifying drugs. Corticosteroids have a short onset of action, but many disease modifying drugs take several weeks or months to demonstrate a clinical effect. These agents include methotrexate, leflunomide (Arava™), etanercept (Enbrel™), infliximab (Remicade™), adalimumab (Humira™), anakinra (Kineret™), rituximab (Rituxan™), CTLA4-Ig (abatacept), antimalarials, gold salts, sulfasalazine, d-penicillamine, cyclosporin A, cyclophosphamide azathioprine; and the like. Disease modifying anti-rheumatoid drugs, or DMARDs have been shown to alter the disease course and improve radiographic outcomes in RA.

Biological agents include inhibitors of tumor necrosis factor, a pro-inflammatory cytokine produced by macrophages and lymphocytes. It is found in large quantities in the rheumatoid joint and is produced locally in the joint by synovial macrophages and lymphocytes infiltrating the joint synovium. The strategies for inhibiting TNF that have been most extensively studied to date consist of monoclonal anti-TNF antibodies and soluble TNF receptors (sTNF-R). Both constructs will bind to circulating TNF-α, thus limiting its ability to engage cell membrane-bound TNF receptors and activate inflammatory pathways. Only approximately ⅓ of patients exhibit a robust clinical response following initiation of any one of the 3 FDA-approved anti-TNF therapies (etanercept, adalimumab and remicade). A second ⅓ of patients experience a partial response to any one of the FDA approved agents, approximately an ACR20 response. The remaining ⅓ of RA patients exhibit no meaningful clinical response when initiated on an approved anti-TNF therapy.

Anakinra (KINERET™) is a human recombinant IL-1 receptor antagonist (hu rIL-1ra) approved by the FDA for the treatment of RA. Anakinra can be used alone or in combination with DMARDs other than TNF blocking agents (Etanercept, Infliximab). Anakinra is a recombinant, nonglycosylated form of the human IL-1ra. It differs from the native nonglycosylated IL-1 ra by the addition of an N-terminal methionine. Anakinra blocks the biologic activity of IL-1 by binding to IL-1R type I with the same affinity as IL-18. Usual time to effect is 2 to 4 weeks.

CTLA4Ig is a genetically engineered fusion protein that consists of a human CTLA4 portion fused to a constant IgG1 region (also known as Abetacept, produced by Bristol-Myers Squib, New York City, New York, USA). Abetacept was approved by the US Food and Drug Administration for the treatment of RA. Only a minority of patients who had failed anti-TNF therapy exhibited significant clinical improvement in response to CTLA4-Ig therapy.

Rituximab (Roche Pharmaceuticals, Basel, Switzerland; Genentech, South San Francisco, USA; IDEC Pharmaceuticals, San Diego, USA), a genetically engineered human-mouse chimeric monoclonal antibody against the CD20 antigen, binds to the CD20 antigen on the B cell surface and efficiently depletes B cells by antibody-dependent and complement-dependent cell lysis. Therapeutic monoclonal antibodies directed against other B cell surface antigens such as CD19, CD21 and CD22 are currently under development. A minority of patient who failed anti-TNF therapy exhibited an ACR50 or greater response to rituximab therapy.

Agents targeting other cytokines, including IL-6, IL-12, IL-15, IL-18, and p19 subunit of IL-23 (Eli Lilly) are in clinical development, as well as agents that target integrins, BlyS, and other markers.

A 56-week Combination Therapy in Rheumatoid Arthritis (COBRA) trial demonstrated that step-down combination therapy with prednisolone, methotrexate, and sulfasalazine (SSZ) was superior to SSZ monotherapy for suppressing disease activity and progression of rheumatoid arthritis (RA). (COBRA: *Arthritis Rheum.* 2002 February; 46(2):347-56). In a follow up study, it was determined that after adjustment for differences in treatment and disease activity during follow-up, the differences between combination therapy-treated and control groups in regard to the rate of progression was statistically significant for each single year of follow up (4-5 years). Independent baseline predictors of radiological progression over time were rheumatoid factor positivity, radiographic scores (Sharp scores), and disease activity score (DAS28). The authors conclude that an initial 6-month cycle of intensive combination treatment that included high-dose corticosteroids resulted in sustained suppression of the rate of radiologic progression in patients with early RA, independent of subsequent anti-rheumatic therapy. The impressive results of this study suggest that aggressive combination therapy very early in the course of RA provides long-term benefit.

The BeST study focuses on different combinations of established DMARDs in conjunction with the TNF blocker infliximab (BeSt Study: *Arthritis Rheum.* 2005 November; 52(11):3381-90). This study aimed at comparing the efficiency of four treatment approaches to minimize disease progression in patients with early RA. An important finding from the study is that similar clinical outcomes were achieved in all treatment groups when patients were followed by Disease Active Score (DAS) scoring and therapy was changed based on a protocol established before the trial had started. As underscored by previous clinical studies, rheumatologists need to quantify disease activity in response to therapy, regardless of which therapy is chosen. Additional clinical trials in early RA involve a number of the novel biological DMARDs including MTX, anti-TNF agents, and CTLA4-Ig both as individual therapies as well as in combination (e.g. MIX; MTX+anti-TNF; anti-TNF; MTX+CTLA4-Ig; CTLA4-Ig).

Of concern, however, is the potential for overtreatment of the subset of early arthritis patients who will experience a benign disease course. It is well established that a subset of early arthritis patients, including patients with early RA, will experience spontaneous natural remission in the absence of therapeutic intervention. Thus, biomarkers are needed to identify and differentiate such patients from patients who will develop full-blow and/or severe RA. Patients predicted to have benign and naturally remitting RA would likely be treated with NSAIDs and other "low-impact" therapies, while patients predicted to evolve to established RA would be treated more aggressively with DMARD therapy, and patients predicted to develop severe debilitating RA would be treated most aggressively with highly potent DMARD therapy. Such a therapeutic strategy could both reduce the incidence of RA, by reducing the number of patients that progress from early arthritis or RA to established RA, as well as reduce the mortality and morbidity from RA.

Diagnostic and Prognostic Methods

The differential presence of ICCF is shown to provide for prognostic evaluations to detect individuals having clinical subtypes of RA that correspond to disease severity. The correlation with disease severity is demonstrated in juvenile and adult patients. In general, such analytic methods involve determining the presence or level of ICCF in an individual sample, usually a blood derived sample, e.g. blood, serum, plasma, etc. A variety of different assays can be utilized to quantitate the presence of these immune complexes. Many such methods are known to one of skill in the art, including ELISA, protein arrays, eTag system, bead based systems, tag or other array based systems etc. Examples of such methods are set forth in the art, including, inter alia, chip-based capillary electrophoresis: Colyer et al. (1997) J Chromatogr A. 781(1-2):271-6; mass spectroscopy: Petricoin et al. (2002) Lancet 359: 572-77; eTag systems: Chan-Hui et al. (2004) Clinical Immunology 111:162-174; microparticle-enhanced nephelometric immunoassay: Montagne et al. (1992) Eur J Clin Chem Clin Biochem. 30(4):217-22; antigen arrays: Robinson et al. (2002) Nature Medicine, 8:295-301; the Luminex XMAP bead array system (www.luminexcorp.com); and the like, each of which are herein incorporated by reference. Detection may utilize C1q or other reagents that selectively immune complexes, and the presence of fibrinogen may be determined with antibodies that recognize fibrinogen. If desired, citrulline can be measured by various chemical assays.

The measurement of ICCF may be generated from a biological sample using any convenient protocol, for example as described below. The readout may be a mean, average, median or the variance or other statistically or mathematically-derived value associated with the measurement. The readout information may be further refined by direct comparison with the corresponding reference or control pattern. The absolute values obtained under identical conditions will display a variability that is inherent in live biological systems and also reflects individual antibody variability as well as the variability inherent between individuals.

Following obtainment of the ICCF measurement from the sample being assayed, the data is compared with a reference or control profile to make a prognosis regarding the phenotype of the patient from which the sample was obtained/derived. Typically a comparison is made with a sample or set of samples from an unaffected, normal source.

Various immunoassays designed to quantitate immune complexes may be used in screening. For example, a conventional sandwich type assay may be used in an array, ELISA, RIA, etc. format. A sandwich assay may first attach a binding member, e.g. C1q, anti-C1q, etc., to an insoluble surface or support. The particular manner of binding is not crucial so long as it is compatible with the reagents and overall methods of the invention. They may be bound to the plates covalently or non-covalently.

The insoluble supports may be any compositions to which polypeptides can be bound, which is readily separated from soluble material, and which is otherwise compatible with the overall method. The surface of such supports may be solid or porous and of any convenient shape. Examples of suitable insoluble include slides, beads, e.g. magnetic beads, membranes and microtiter plates. These are typically made of glass, plastic (e.g. polystyrene), polysaccharides, nylon or nitrocellulose.

Patient sample preparations are then added to the substrate. Preferably, a series of standards, containing known concentrations of the immune complex is assayed in parallel with the samples or aliquots thereof to serve as controls. Preferably, samples are assayed in multiple spots, wells, etc. so that mean values can be obtained for each. The incubation time should be sufficient for binding, generally, from about 0.1 to 3 hr is sufficient. After incubation, the insoluble support is generally washed of non-bound components. A dilute non-ionic detergent medium at an appropriate pH, generally 7-8, can be used as a wash medium. From one to six washes can be employed, with sufficient volume to thoroughly wash non-specifically bound proteins present in the sample.

After washing, a solution containing a detection reagent, e.g. antibodies reactive with human immunoglobulin, or antibodies reactive with fibrinogen is applied. The second stage reagent may be labeled to facilitate direct, or indirect quantification of binding. Examples of labels that permit direct measurement of second receptor binding include radiolabels, such as $^3$H or $^{125}$I, fluorescers, dyes, beads, chemiluminescers, colloidal particles, and the like. Examples of labels that permit indirect measurement of binding include enzymes where the substrate may provide for a colored or fluorescent product. In a preferred embodiment, the antibodies are labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. The incubation time should be sufficient for the labeled ligand to bind available molecules. Generally, from about 0.1 to 3 hr is sufficient, usually 1 hr sufficing.

After the second binding step, the insoluble support is again washed free of non-specifically bound material, leaving the specific complex formed between the immune complexes and the detection reagent. The signal produced by the bound conjugate is detected by conventional means. Where an enzyme conjugate is used, an appropriate enzyme substrate is provided so a detectable product is formed.

Other immunoassays are known in the art and may find use as diagnostics. Ouchterlony plates provide a simple determination of antibody binding. Western blots may be performed on protein gels or protein spots on filters, using a detection system specific for the immune complexes, conveniently using a labeling method as described for the sandwich assay.

In some cases, a competitive assay will be used. In addition to the patient sample, a competitor to the immune complex is added to the reaction mix. The competitor and the immune complex compete for binding. Usually, the competitor molecule will be labeled and detected as previously described, where the amount of competitor binding will be proportional to the amount of target present. The concentration of competitor molecule will be from about 10 times the maximum anticipated protein concentration to about equal concentration in order to make the most sensitive and linear range of detection.

Alternatively, a reference sample may be used as a comparator. In such a case, the reference patient sample is labeled with or detected using a spectrally distinct fluorophore from that used to label or detect immune complexes from the patient sample. This reference sample is mixed with the patient sample, and the mixed sample analyzed by immune complex measurement methodology. Such an approach provides a ratio of patient:reference sample binding, thereby enabling direct comparative analysis of patient sample relative to reference sample binding.

Kits and Devices

Also provided are reagents and kits thereof for practicing one or more of the above-described methods. The subject reagents and kits thereof may vary greatly. Reagents of interest include reagents specifically designed for use in production of the above described analysis of circulating immune complexes associated with RA. Such devices or kits will include reagents that specifically identify fibrinogen immune complexes as described above. The reagents may be provided as a kit comprising reagents in a suspension or suspendable form, e.g. reagents bound to beads suitable for flow cytometry, and the like. Reagents of interest include reagents specific for fibrinogen and immune complexes.

In this type of "tag array," where the antigen is bound to beads or microspheres, one may utilize flow cytometry for detection of binding. For example, microspheres having fluorescence coding have been described in the art, where the color and level of fluorescence uniquely identifies a particular microsphere. The antigen is thus covalently attached to a "color coded" object. A labeled antibody can be detected by flow cytometry, and the coding on the microsphere used to identify the bound antigen.

In yet another embodiment, surface plasmon resonance (SPR) imaging is utilized to detect immune complex binding without the need for fluorescent, enzymatic, or other detection markers. SPR, which senses refractive index change of molecules bound to a metal surface, provides label-free detection for immune complex binding, which eliminates additional reaction and washing steps associated with most conventional detection methods.

The kits may further include a software package for statistical analysis of one or more phenotypes, and may include a reference database for calculating the probability of prognosis. The kit may include reagents employed in the various methods, such as devices for withdrawing and handling blood samples, second stage antibodies, ELISA reagents; tubes, spin columns, and the like.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, hard-drive, network data storage, etc., on which the information has been recorded. Yet another means that may be present is a website address which may be used via the internet to access the information at a removed site. Any convenient means may be present in the kits.

Assessment of Patient Outcomes

Patient outcomes prognosis may be assessed using imaging-based criteria such as radiographic scores, clinical and laboratory criteria. Multiple different imaging, clinical and laboratory criteria and scoring systems have been and are being developed to assess disease activity and response to therapy in rheumatoid arthritis.

In rheumatoid arthritis, response to therapy is conventionally measured using the American College of Rheumatology (ACR) Criteria. The ACR response criteria are a composite score comprising clinical (swollen joint count, tender joint count, physician and patient response assessment, and health assessment questionnaire), and laboratory (acute phase response) parameters; level of improvement is reported as an ACR20 (20%), ACR50 (50%) or ACR70 (70%) response, which indicates percent. change (improvement) from the baseline score. A number of clinical trails based on which the anti-TNFα agents infliximab (Remicade™), etanercept (Enbrel™) and adalimumab (Humira™) were approved to treat human RA utilized ACR response rates as a primary outcome measure.

Responses in rheumatoid arthritis many also be assessed using other response criteria, such as the Disease Activity Score (DAS), which takes into account both the degree of improvement and the patient's current situation. The DAS has been shown to be comparable in validity to the ACR response criteria in clinical trials. The definitions of satisfactory and unsatisfactory response, in accordance with the original DAS and DAS28. The DAS28 is an index consisting of a 28 tender joint count, a 28 swollen joint count, ESR (or CRP), and an optional general health assessment on a visual analogue scale (range 0-100) (Clinical and Experimental Rheumatology, 23(Suppl. 39):S93-99, 2005). DAS28 scores are being used for quantification of response mostly in European trials of (early) rheumatoid arthritis such as the COBRA or BeST studies.

Radiographic measures for response in RA include both conventional X-rays (plain films), and more recently magnetic resonance (MR) imaging, computed tomography (CT), ultrasound and other imaging modalities are being utilized to monitor RA patients for disease progression. Such techniques are used to evaluate patients for inflammation (synovitis), joint effusions, cartilage damage, bony erosions and other evidence of joint damage. Methotrexate, anti-TNF agents and DMARD combinations have been demonstrated to reduce development of bony erosions and other measures of joint inflammation and destruction in RA patients. In certain cases, such as with anti-TNF agents, healing of bony erosions has been observed.

Animal Models

Non-human animal models for rheumatoid arthritis are provided. The models are useful for testing and screening of biologically active agents for the treatment of RA. In the fibrinogen induced arthritis (FIA) model described herein, the native form of fibrinogen is used as the immunizing antigen. FIA involves robust T-cell reactivity to native fibrinogen and B-cell reactivity to native fibrinogen, citrullinated fibrinogen, and other candidate RA autoantigens. Disease can be transferred with either fibrinogen-reactive T cells or plasma from FIA mice. Mice with FIA possess RF, anti-CCP antibodies, and IgG immune complexes, all of which are characteristic of a subset of RA patients. Compared to the arthritis that develops in other murine models of RA, FIA is mild to moderate and therefore more closely resembles human RA, and provide a useful model for the development of RA, and for drug/gene screening in the prevention and treatment of chronic inflammatory disease in humans. Another advantage of the FIA model is that it does not rely on genetically altered mice expressing a TCR-encoding transgene or mutated form of CD45, but rather uses wild-type mice.

A host animal susceptible to induced autoimmune disease, e.g. DBA/1; SJL mice, is immunized with a dose of human fibrinogen, delivered enterally or parenterally, e.g., subcutaneously, cutaneously, intramuscularly, intradermally, intravenously, intraarterially, intraperitoneally, intranasally, orally, intraheart, intrapancreas, intraarticular, etc. Sub-cutaneous delivery is preferred. The fibrinogen may be isolated from other proteins present in serum, and may be wild-type or experimentally altered, e.g. by increasing or decreasing the citrullation and other post-translational processing. The initial dose will comprise at least about 0.05 mg fibrinogen/mouse, at least about 0.1 mg fibrinogen/mouse, at least about 0.5 mg fibrinogen/mouse, and usually not more than about 5 mg fibrinogen/mouse. The initial dose is generally administered with an adjuvant. Many suitable adjuvants are known in the art, e.g. emulsions such as complete Freund's adjuvant (CFA), incomplete Freund's adjuvant (IFA), etc., MF59, or SAF; mineral gels such as aluminum hydroxide (alum, for example, Al(OH)3 reHydragel® available from Reheis, Berkley Heights, N.J.)), aluminum salts (e.g., aluminum phosphate) or calcium salts (e.g., calcium phosphate); microbially-derived adjuvants such as cholera toxin (CT), pertussis toxin, *Escherichia coli* heat-labile toxin (LT), mutant toxins (e.g., LTK63 or LTR72), Bacille Calmette-Guerin (BCG), lipopolysaccharides (LPS), mycobacteria, tetanus toxin, *Corynebacterium parvum*, DNA CpG motifs, muramyl dipeptide, or monophosphoryl lipid A; particulate adjuvants such as immunostimulatory complexes (ISCOMs), liposomes, biodegradable microspheres, or saponins (e.g., QS-21); cytokines such as IFN-γ, IL-2, IL-12 or GM-CSF; synthetic adjuvants such as nonionic block copolymers or surfactants, muramyl peptide analogues (e.g., N-acetyl-muramyl-L-threonyl-D-isoglutamine [thr-MDP], N-acetyl-normuramyl-L-alanyl-D-isoglutamine, N-acetylmuramyl-L-alanyl-D-isoglutaminyl-L-alanine-2-[1'-2'-dipalmitoyl-sn-glycero-3-hydroxyphosphoryloxy]-ethylamine), polyphosphazenes, synthetic polynucleotides, surface active substances such as lysolecithin, pluronic polyols, polyanions, peptides, hydrocarbon emulsions, or keyhole limpet hemocyanins (KLH), and the like as known in the art. The animal may be boosted with a second dose after a suitable interval, e.g. from 2 to 4 weeks.

These animals provide a useful model for the requirements RA initiation and pathogenesis. By providing a more accurate model for the human disease, potential therapeutics can be evaluated in the animal model for safety and efficacy prior to clinical trials. In addition to screening candidate pharmaceutical agents, the subject animals are useful in determining the role of "triggering" agents in development of disease, the role of specific T cell subsets and cytokines, and the role of specific antigens in activation and maintenance of RA.

Generally, the host will be at least about four weeks old. For example, mice are often used at about 4 to 12 weeks of age. The mammalian host will be grown in conventional ways.

Disease can also be transferred from one animal expressing disease to another naive animal by extracting effector cells from the diseased animal and injecting them into multiple naive animals. In one embodiment, a secondary transfer is performed, where whole spleen or lymph node cells from a primary host that was previously immunized with fibrinogen, are transferred into a secondary host. The primary host may be diseased or not-diseased. The cells from the primary host may be unfractionated spleen, lymph node, etc. Alternatively, disease can be transferred with plasma or purified antibodies and immune complexes.

The population of T cells or antibodies are injected into a recipient. Routes of administration include systemic injection, e.g. intravascular, subcutaneous, or intraperitoneal injection. Where the recipient animal is a mouse, the number of cells injected will usually be at least about $0.5 \times 10^5$ and not more than about $5 \times 10^5$, more usually at least about $1 \times 10^5$, preferably between about $3 \times 10^5$ and $4 \times 10^5$. Where the recipient animal is a larger animal, the number of cells will be increased accordingly.

After immunization, within about 4 to 8 weeks the animals develop rheumatoid arthritis disease. Scoring of the disease severity is based on physical appearance, histology, presence of disease associated antibodies and immune complexes, cytokine expression, presence of T cells at the lesion, etc.

To more fully characterize the disease, immunophenotypic analysis may be performed to detect a variety of relevant antigenic determinants. To characterize the types of immune cells present, immunohistochemical stains for various leukocyte markers may be performed. The expression of additional adhesion molecules that are relevant to the pathophysiology of chronic inflammatory disease may include mononuclear cell infiltrate; T cells at lesions; and the expression in adjacent blood vessels of focal E-selectin, P-selectin, ICAM-1 and diffuse vascular cell adhesion molecule-1 (VCAM-1) expression.

The subject animals are useful for screening candidate therapeutic agents and treatment modalities. Through use of the subject animals or cells derived therefrom, one can identify ligands or substrates that affect the progression of rheumatoid arthritis. Of particular interest are screening assays for agents that have a low toxicity for human cells.

Drug screening protocols will generally include a panel of animals, for example a test compound or combination of test compounds, and negative and/or positive controls, where the positive controls may be known immunosuppressive agents. Such panels may be treated in parallel, or the results of a screening assay may be compared to a reference database.

A wide variety of assays may be used for this purpose, including histological analysis of effectiveness, determination of the localization of drugs after administration, labeled in vitro protein-protein binding assays, protein-DNA binding assays, electrophoretic mobility shift assays, immunoassays for protein binding, and the like. Depending on the particular assay, whole animals may be used, or cells derived therefrom. Cells may be freshly isolated from an animal, or may be immortalized in culture. Candidate therapies may be novel, or modifications of existing treatment options.

For screening assays that use whole animals, a candidate agent or treatment is applied to the subject animals. Typically, a group of animals is used as a negative, untreated or placebo-treated control, and a test group is treated with the candidate therapy. Generally a plurality of assays are run in parallel with different agent dose levels to obtain a differential response to the various dosages. The dosages and routes of administration are determined by the specific compound or treatment, to be tested, and will depend on the specific formulation, stability of the candidate agent, response of the animal, etc.

The analysis may be directed towards determining effectiveness in prevention of disease induction, where the treatment is administered before induction of the disease. Alternatively, the analysis is directed toward regression of existing lesions, and the treatment is administered after initial onset of the disease, or establishment of disease. Frequently, treatment effective for prevention is also effective in regressing the disease.

In either case, after a period of time sufficient for the development or regression of the disease, the animals are assessed for impact of the treatment, by visual, histological, immunohistological, and other assays suitable for determining effectiveness of the treatment. The results may be expressed on a semi-quantitative or quantitative scale in order to provide a basis for statistical analysis of the results.

The term "agent" as used herein describes any molecule, e.g. protein or pharmaceutical, with the capability of affecting the severity of rheumatoid arthritis. An agent or treatment is administered to an animal of the invention, or to cells derived therefrom. Antibodies specific for cytokines, and autoantigens are agents of particular interest. Most preferably, according to another aspect of the instant invention, the agents are monoclonal antibodies, e.g. which neutralize cytokines or block adhesion molecules.

Other candidate agents encompass numerous chemical classes, typically organic molecules. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

The therapeutic agents may be administered to patients in a variety of ways, orally, topically, parenterally e.g. subcutaneously, intramuscularly, intravascularly, etc. Depending upon the manner of introduction, the compounds may be formulated in a variety of ways. The concentration of therapeutically active agent in the formulated pharmaceutical compositions may vary from about 0.1-100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. All technical and scientific terms used herein have the same meaning as commonly understood to one of ordinary skill in the art to which this invention belongs unless clearly indicated otherwise.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

All publications and patent applications cited in this specification are herein incorporated by reference as if each individual publication or patent application were specifically and individually indicated to be incorporated by reference.

EXPERIMENTAL

Example 1

RA is characterized by excessive generation and breakdown of fibrinogen. Further, the citrullinated α- and β-chains of fibrin have been identified as a potential target of the autoantibody response in RA, and citrullinated fibrinogen has been identified in synovial fluid derived from RA patients. Autoantibodies against citrullinated fibrinogen have been described to provide diagnostic value in arthritis. We adapted C1q capture immunoassays to utilize fibrinogen-specific secondary antibodies to identify fibrinogen-containing immune complexes, and applied these immunoassays to plasma samples derived from RA and control patients.

We further investigate the targets of the autoantibody response and the antigens incorporated in immune complexes (IC) in RA. We demonstrate that one-half of CCP+ RA patients possess circulating (blood) ICs containing citrullinated fibrinogen. This subgroup of RA also possessed increased autoantibodies targeting citrullinated fibrinogen. Fractionation of whole RA plasma revealed citrullinated fibrinogen in the high molecular weight fractions that contained immune complexes. Positive correlations were observed between citrullinated-fibrinogen containing immune complexes and anti-citrullinated fibrinogen autoantibodies, anti-CCP antibody, rheumatoid factor and certain clinical characteristics. Immunohistochemical staining demonstrated co-localization of fibrinogen, immunoglobulin and complement component C3 in pannus tissue derived from RA patients. Further, mass spectrometry identified citrullinated fibrinogen peptides in immune complexes immunoprecipitated from lysates of RA pannus tissue. These data show that autoantibody targeting of citrullinated fibrinogen results in the formation of fibrinogen-containing ICs that characterize a subset of CCP+ RA patients and may contribute to synovitis in RA.

Materials and Methods

Human samples. All RA and control plasma and joint samples were obtained and studied with informed consent under IRB approved protocols. The plasma samples utilized came from the Multiple Autoimmune Disease Genetics Consortium (MADGC) and the Stanford Arthritis Center, collected with EDTA tubes (Table1). The diagnosis of RA was made based on the American College of Rheumatology 1987 criteria.

TABLE 1

Source and description of samples used in the study.

| Sample source | Disease | No. | Female, no. (%) | Age (range) | CCP positive, no. (%) | RF positive, no. (%) |
|---|---|---|---|---|---|---|
| Dr. P. Gregersen, plasma set 1 | RA | 30 | 28 (93) | 72.6 (51-89) | 20 (67) | 24 (80) |
| | Healthy | 10 | | | | |

TABLE 1-continued

Source and description of samples used in the study.

| Sample source | Disease | No. | Female, no. (%) | Age (range) | CCP positive, no. (%) | RF positive, no. (%) |
|---|---|---|---|---|---|---|
| Dr. P. Gregersen, plasma set 2 | IBD | 20 | 13 (65) | 46.4 (23-82) | 6 (30) | 6 (30) |
| | JRA | 20 | 16 (80) | 37.3 (10-71) | | |
| | PsA | 14 | 11 (79) | 52.6 (23-75) | | |
| | PS | 20 | 10 (50) | 55.3 (22-86) | | |
| | RA | 20 | 19 (95) | 59.0 (35-89) | | |
| | SLE | 20 | 13 (65) | 51.3 (29-67) | | |

CCP = cyclic-citrullinated peptides; RF = rheumatoid factor; RA = rheumatoid arthritis; IBD = inflammatory bowel disease; JRA = juvenile rheumatoid arthritis; PsA = psoriatic arthritis; PS = psoriasis; SLE = systemic lupus erythematosus.

Mass spectrometry analysis. For in-gel digestion, protein spots were excised from the gel and treated with trypsin overnight at 37° C. The tryptic peptides were resolved by HPLC using a Zorbax 300SB-C18 nanocolumn packed with 3.5 µm particles (Agilent Technologies) and eluted at 300 nL/min with a 60-min linear gradient from 0 to 95% acetonitrile containing 0.1% formic acid. Separated peptides were electrosprayed into an ion trap mass spectrometer (XCT Plus, Agilent Technologies). For ICs immunoprecipitated from RA pannus tissue lysates, the precipitated complexes were directly digested with trypsin before mass spectrometry analysis. Proteins were identified based on raw MS/MS data compared to a SwissProt database using Mascot (Matrix Science) with valid peptide hits.

Detection of anti-citrullinated fibrinogen autoantibodies. Native fibrinogen (Calbiochem) was citrullinated in vitro with a peptidylarginine deiminase (PAD) derived from rabbit skeletal muscle (Sigma) using protocols previously described. Anti-citrullinated fibrinogen autoantibodies were assayed as previously described by others. Briefly, native fibrinogen or citrullinated fibrinogen was coated on ELISA plates (MaxiSorp, Nunc, Rochester, N.Y.) overnight at 4° C. at a concentration of 20 µg/mL. Subsequent incubations and washes were done at room temperature. The plates were blocked with 3% BSA in PBST (0.05% Tween-20) for 1 hour, washed, and incubated with centrifuged plasma (diluted 50-fold) on a shaker for 1.5 hour. Anti-fibrinogen autoantibody was detected using HRP-conjugated secondary reagents specific for human IgG (γ chain) or IgM (µ chain) specific antibodies diluted 1:20,000.

Quantitation of immune complexes. ELISA plates were coated with 20 µg/mL C1q (Sigma) in PBS overnight at 4° C. Subsequent incubations and washes were done at room temperature. The plates were blocked with 3% BSA in PBST (0.05% Tween-20) for 1 hour. After washing, plasma from RA patients or healthy controls were diluted 1:50 in PBST and incubated on a shaker for 1.5 hours. ICs were detected with HRP-conjugated rabbit antiserum specific for human IgG or IgM (Jackson Immunoresearch).

Quantitation of fibrinogen-containing immune complexes. C1q coated ELISA plates were blocked with 3% BSA in PBST for 1 hour. After washing, plasma from RA patients or healthy controls was diluted 1:10 and incubated on a shaker for 1.5 hour. Fibrinogen contained within the captured ICs was detected using a 1:4000 dilution of HRP-conjugated rabbit anti-human fibrinogen antiserum (DAKO).

Anti-CCP and RF (IgM) ELISA. The CCP (Euro Diagnostica, Sweden) and RF ELISA kits (Alpha Diagnostic International, San Antonio, Tex.) were used according to the manufacturer's protocol, except that plasma was used instead of serum. CCP and RF values of the samples were expressed as IU/mL.

Fractionation of plasma samples. The plasma samples were filtered by a 0.45 µm cellulose acetate membrane in a Spin-x centrifuge tube filter (Corning, N.Y.) to remove cell debris and precipitates. A volume of 150 µL of the filtered plasma sample was injected to a fast protein liquid chromatography (FPLC) system (Pharmacia LKB Biotechnology) equipped with a Superdex 200 10/300 gel filtration column (Amersham Biosciences). A mixture of protein standard containing human fibrinogen, human albumin and IgG was run in parallel to further identify different peaks. All liquid chromatography runs were programmed at 0.4 mL/min flow rate with a PBS buffer and fractions of 0.5 mL were collected. To measure total protein content of the fractions, 20 µL of each fraction was mixed with 100 µL of BCA buffer (Pierce Biotechnology, Ill.) and the mixture was incubated at 37° C. for 30 min before the results were read at 562 nm on a spectraMAX190 instrument (Molecular Devices). To measure IgG and fibrinogen ICs, 50 µL of each fraction was applied to the C1q ELISA described above. To measure total IgG and fibrinogen content, the fractions were first diluted 10-fold with PBS. Then 14 of the dilutes was deposited onto a nitrocellulose membrane and let dry overnight. After blocking with 5% milk in PBST, HRP conjugated anti-human IgG or anti-human fibrinogen was applied to the membranes. Detection was done with SuperSignal West Pico Substrate (Pierce Biotechnology, Ill.). The densitometry of exposed film were measured with Fluor Chem imaging system (Alpha Innotech, Calif.).

Immunoblot. Plasma fractions were further separated with Precast Criterion Tris-HCl gels (4-20% linear gradient, Bio-Rad), and separated proteins blotted onto nitrocellulose membranes. After blocking with 3% BSA in phosphate buffered saline (PBS), sera from RA patients or healthy controls were used to probe the membranes. Bound antibodies were detected with HRP-conjugated anti-human IgG (Jackson Immunoresearch) using a SuperSignal kit (Pierce) and chemiluminescence was imaged with Fluor Chem imaging system (Alpha Innotech). Immunoblot with anti-modified citrulline was done with an anti-citrulline detection kit (Upstate, Chicago, Ill.) according to manufacturer's instructions.

Immunohistochemistry. Slides were deparaffinized and hydrated to water, endogenous peroxidase was inhibited with 3% $H_2O_2$, and nonspecific staining blocked with DAKO Protein Block Serum-Free (Dako, Carpinteria, Calif.). Staining for complement C3 was performed using a 1:2000 dilution of rabbit polyclonal against human complement C3 (Dako, Carpinteria, Calif.). For fibrinogen and IgG staining, pretreatment of proteinase K was utilized prior to the primary antibody incubation (Dako, Carpinteria, Calif.). Slides positive for fibrinogen were immunohistochemically stained with a rabbit polyclonal against human fibrinogen (Dako, Carpinteria, Calif.), RT 1:1600 for 30 minutes. After incubation with primary antibody, the tissue sections were sequentially incubated with Dako Envision+Rabbit System Labeled Polymer HRP (Dako, Carpinteria, Calif.) or biotinylated rabbit anti-goat antibodies (Vector, Burlingame, Calif.) followed by streptavidin HRP (Dako, Carpinteria, Calif.). Staining was developed with Liquid DAB+ (Dako, Carpinteria, Calif.) and counterstained with Hematoxylin.

Statistics. All statistics were run using InStat™ software (GraphPad Software Inc., San Diego, Calif.). For quantitation of ICs and autoantibodies to fibrinogen, unpaired t-tests with Welch correction were used.

Results

Identification of fibrinogen-containing circulating ICs in RA. C1q binds aggregated immunoglobulin Fc regions, and has been used to capture and quantitate ICs. We utilized C1q capture immunoassays and HRP labeled secondary antibodies specific for human IgG and IgM to quantitate circulating ICs in plasma derived from CCP+ RA, CCP− RA and healthy controls (FIG. 1A,B). Elevated circulating IgG ($p=0.01$; FIG. 1A) and IgM ($p=0.0002$; FIG. 1B) ICs were observed in CCP+ RA patients as compared to healthy controls. Most CCP− RA patients did not possess circulating. ICs (FIG. 1A,B).

To determine if circulating ICs containing fibrinogen are present in RA, following C1q capture a fibrinogen-specific secondary antibody was used. One-half of CCP+ RA patients possessed fibrinogen-containing ICs as compared to healthy controls ($p=0.0004$) and CCP− RA patients ($p=0.0008$) (FIG. 1C). CCP+ RA patients showed elevated titers of fibrinogen-containing ICs relative to CCP− RA and healthy controls with low standard deviations (FIG. 1E).

To further demonstrate that the observed fibrinogen-containing ICs did not result from non-specific binding of fibrinogen to immobilized C1q, we immobilized anti-C1q monoclonal antibody to capture the C1q-bound ICs followed by detection with anti-fibrinogen antibodies. Similar results were obtained with anti-C1q monoclonal antibody capture as compared to C1q capture of ICs, and yielded a $R^2$ value of 0.9 in linear regression analysis of the two assays (data not shown). Fibrinogen-containing ICs were also analyzed from freshly collected plasma samples from both CCP+ RA and CCP− RA patients (within 2 hours of blood draw using EDTA plasma collection tubes). Compared to the same samples after a freeze-thaw cycle, no difference was detected (FIG. 1F).

To demonstrate that fibrinogen containing ICs were specifically detected in RA compared to other autoimmune diseases, these ICs were analyzed from plasma samples collected in a panel of healthy (n=10), inflammatory bowel disease (IBD, n=20), juvenile rheumatoid arthritis (JRA, n=20), psoriatic arthritis (PsA, n=14), psoriasis (PS, n=20), systemic lupus erythematosus (SLE, n=20), and RA (n=20) patients (FIG. 1D). A subset of RA and a small subset of JRA patients exhibited elevated circulating ICs containing fibrinogen, while patients with other autoimmune diseases did not (FIG. 1D). The subset of JRA patients possessing circulating ICs containing fibrinogen also possessed anti-citrullinated fibrinogen antibodies, RF and anti-CCP antibodies (Table 2). Chart reviews performed on this subset of JRA patients revealed that these patients exhibited symmetrical polyarthritis (Table 2). These observations suggest that this subset of "JRA" patients in fact have adult RA, and is consistent with prior reports of 13% of JRA patients exhibiting anti-CCP antibodies and clinical features consistent with adult RA.

Liquid chromatographic separation demonstrates co-fractionation of citrullinated fibrinogen with ICs. To demonstrate that the fibrinogen-containing ICs in plasma are physically distinct from free fibrinogen and free immunoglobulin, we utilized size exclusion chromatography as previously described. Size exclusion chromatography was applied to fractionate plasma derived from an RA patient possessing fibrinogen containing circulating ICs, an RA patient possessing circulating ICs but not fibrinogen-containing circulating ICs, a PsA patient, and a healthy control (FIG. 2A). Forty-five fractions were generated of each patient's plasma, and each fraction was assayed for ICs, fibrinogen-containing ICs, total immunoglobulin (Ig), total fibrinogen and total protein. ELISA analysis of the fractions containing IgG immune complexes showed two peaks in the elution profile of both RA samples, but not in the corresponding fractions from the PsA and healthy control samples (FIG. 2A, green line). The first peak (RA1 and RA2, green line) corresponded to the first three fractions after the void volume, which had a molecular mass of 300 kD or higher, and corresponded to the fractions in which immune complexes eluted. The second peak (RA1 and RA2, green line) corresponded to free IgG as compared to a chromatography run of standards (STD, blue line). ELISA analysis of fibrinogen immune complexes on RA1 (which possessed fibrinogen ICs) showed a single peak (FIG. 2A, RA1, red line) that was eluted in the same fractions at the IgG immune complex peak (FIG. 2A, RA1 and RA2, first peak of green line). Similar analysis on RA2 did not show a co-eluted peak (RA2; red line). To further determine that fibrinogen detected from immune complex fractions is not a contamination from free fibrinogen in blood, free fibrinogen from each RA1 fraction is quantitated by dot assay (FIG. 2A, right panel, pink line). The peak of free fibrinogen was well separated from the peak of fibrinogen immune complex (FIG. 2A, right panel, red line), as shown by the first two dotted lines. Psoriatic arthritis and healthy control patients did not possess circulating ICs (PsA and Healthy, green line). It is possible that following the collection of the plasma fractions, that the free IgG fractions that contained high levels of IgG developed some IgG aggregates that were then detected by our IgG IC assay. These results demonstrate that the fibrinogen-containing circulating ICs observed co-elute with the IgG ICs, and that the fractions containing fibrinogen-ICs are distinct from those containing free fibrinogen and free Ig.

To determine if the fibrinogen present in circulating ICs is citrullinated, the FPLC fractions that contained fibrinogen ICs were separated by SDS-PAGE and immunoblotted with anti-modified citrulline antibody (FIG. 2B). Citrullinated polypeptides that co-migrated with fibrinogen polypeptides were detected only in the fractions derived from RA patients but not in the corresponding fractions isolated from controls. The band, indicated as fibrinogen beta chain, was further analyzed by mass spectrometry. Two distinct citrullinated peptides from the fibrinogen beta chain were identified (FIG. 2C).

Figure 3:
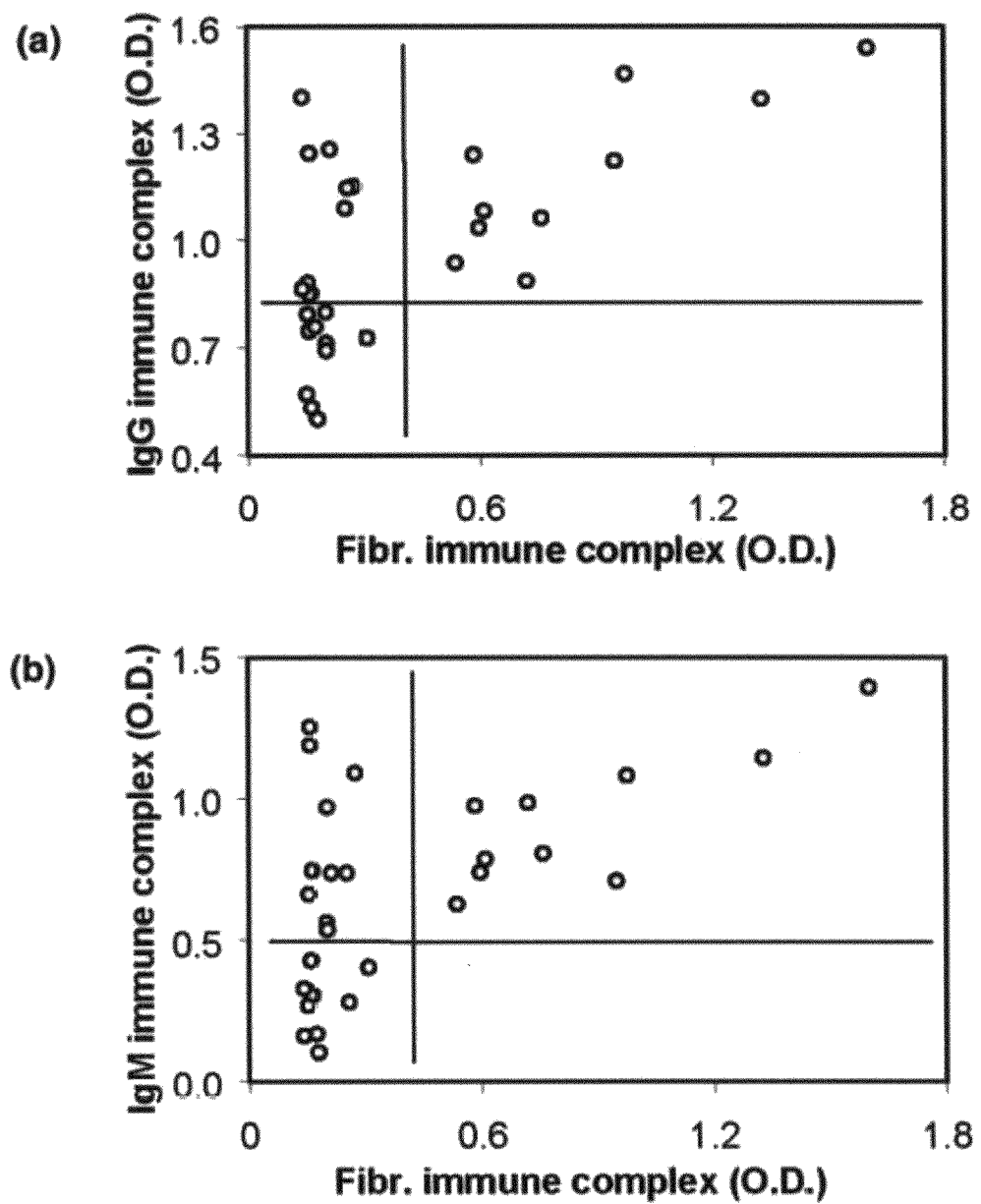
FIG. 3. Fibrinogen-containing circulating ICs are associated with anti-CCP antibodies, RF, and >10 year disease duration. A-F, Scatter plots are presented for the association of fibrinogen ICs with IgG and IgM ICs (A and B), anti-citrullinated fibrinogen antibodies with anti-CCP antibodies (C); fibrinogen ICs with anti-CCP antibodies (D), RF (E), and anti-citrullinated fibrinogen (F). Lines were drawn to mark the negative and positive measurements of each species. G and H, Levels of fibrinogen ICs are also plotted in RA patients with >10 years disease duration (G), and smoking history (H). I, Unsupervised hierarctical clustering of 30 RA patients and levels of fibrinogen circulating ICs, anti-citrullinated fibrinogen antibodies, RF and CCP are presented as a heatmap. Tree dendrograms represent the statistical relatedness between patients.
Figure 3:
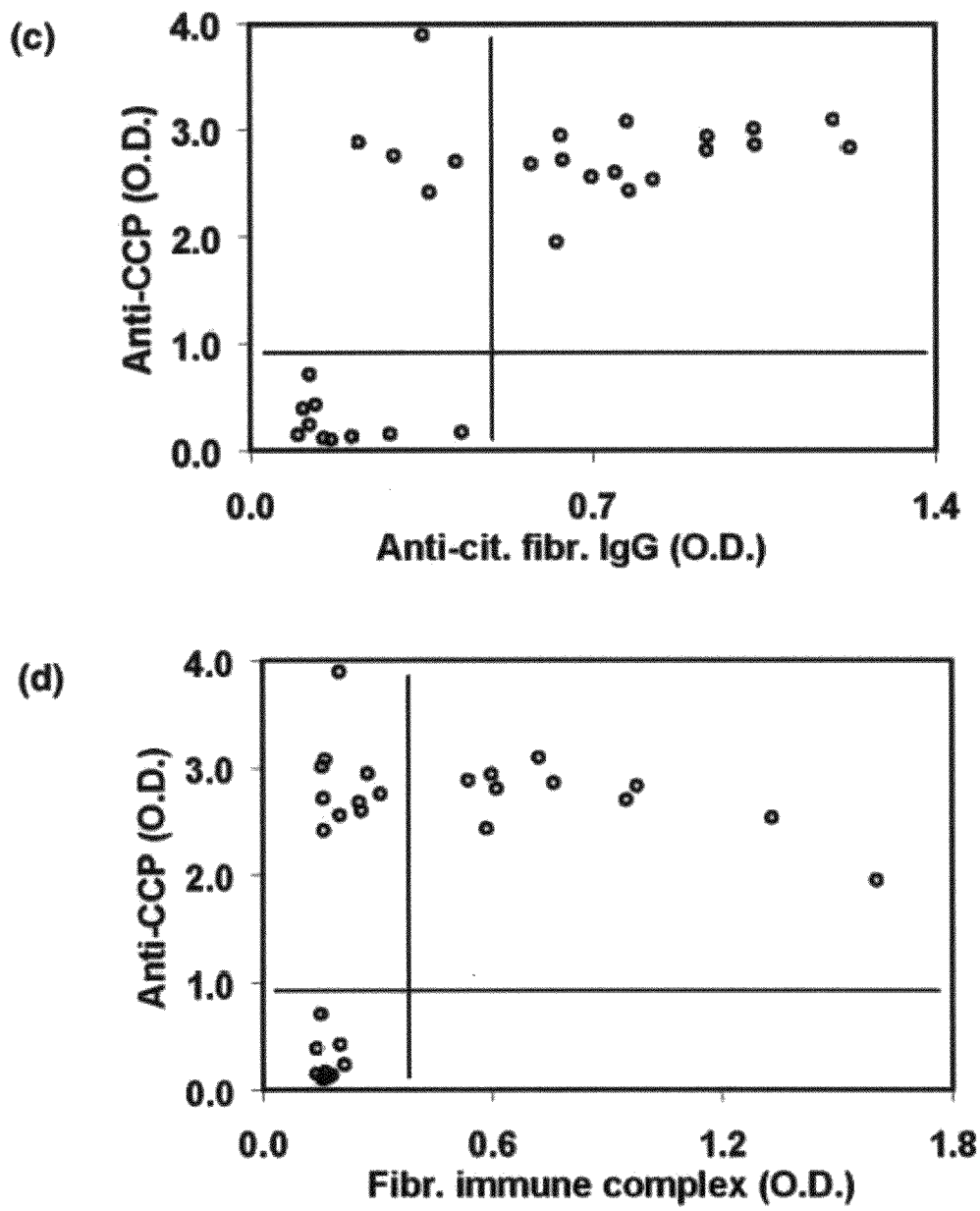
Figure 3:
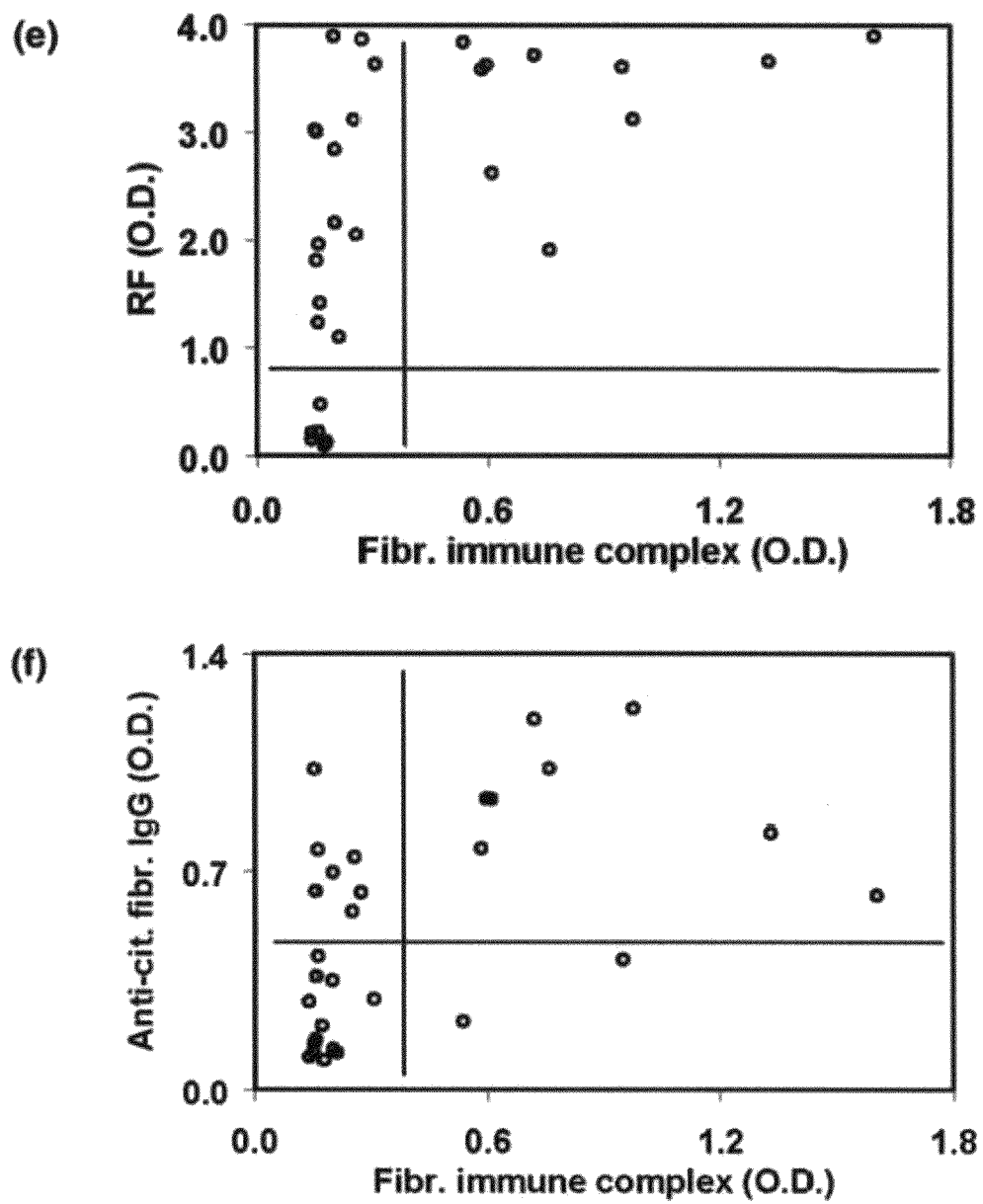
Figure 3:
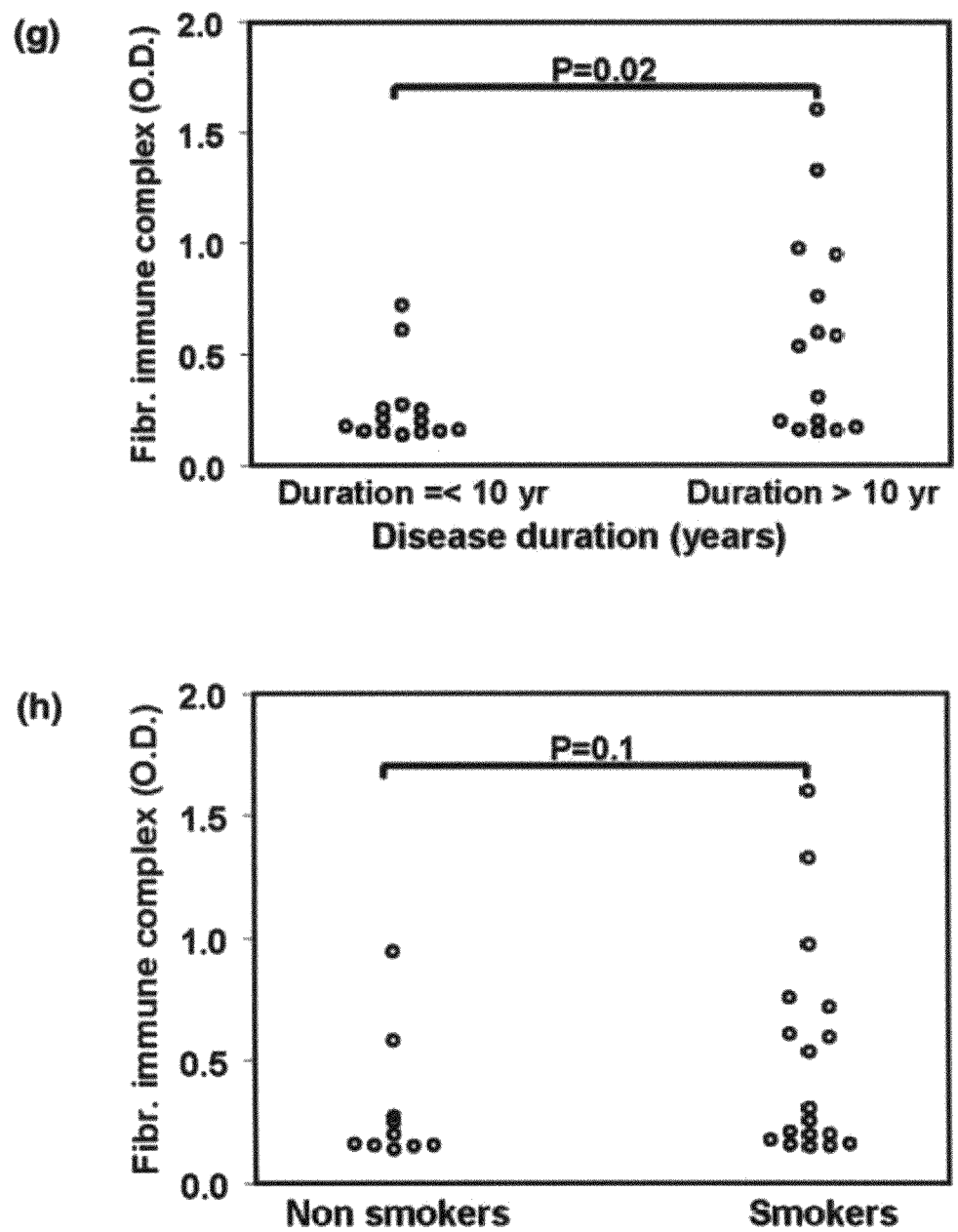
Figure 3:
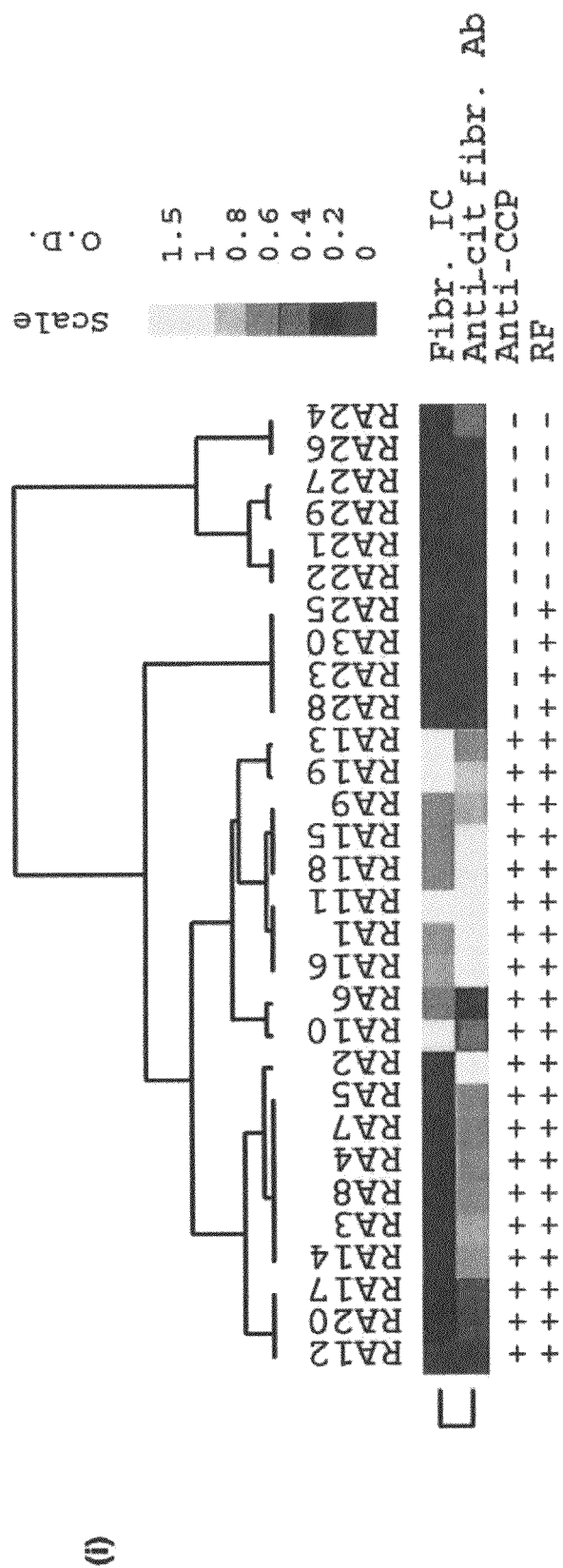

Laboratory and clinical features associated with fibrinogen-containing circulating ICs. We observed positive correlations between fibrinogen-containing ICs with IgG and IgM ICs, anti-citrullinated fibrinogen antibodies, anti-CCP antibodies, rheumatoid factor (RF) and certain clinical characteristics (FIG. 3 A-H). Of CCP+ RA patients, three-quarters possess anti-citrullinated fibrinogen antibodies (FIG. 3 C, I) and one-half possess fibrinogen-containing circulating ICs (FIG. 3D, I). All patients with fibrinogen-containing circulating immune complexes possess RF, while over one-half of RF+ patients did not possess fibrinogen-containing ICs (FIG. 3E, I). Interestingly, fibrinogen containing ICs were not detected in a subset of the RA patients who possessed high IgG and IgM plasma ICs, suggesting that circulating ICs containing other antigens are present in this subset of RA patients (FIG. 3A,B). In RA patients, the presence of circulating ICs containing fibrinogen was associated with disease duration >10 years (p=0.02; FIG. 3G), and there were trends towards associations with smoking (p=0.1; FIG. 3H).

Unsupervised hierarchical clustering of 30 RA patients based on their anti-CCP antibody, RF, anti-citrullinated fibrinogen antibody, and fibrinogen-containing CIC levels demonstrates statistical groupings (FIG. 3I). The CCP+, RF+ patients cluster together, and over half of these patients possess anti-citrullinated fibrinogen autoantibodies and circulating ICs containing fibrinogen.

Immunohistochemistry demonstrates co-staining of fibrinogen, complement component C3, and Ig in pannus tissue derived from RA patients. To further investigate the role of fibrinogen-containing ICs in RA, we performed immunohistochemistry on remnant pannus tissue derived from two CCP+ RF+ RA patients. Pannus tissue was obtained from RA patients at the time of knee arthroplasty, fixed, sectioned, and consecutive sections stained with antibodies specific for complement component C3, fibrinogen and immunoglobulin. Representative results are presented from the analysis of consecutive sections of pannus derived from two independent patients. Immunohistochemical staining demonstrates co-localization of the complement component C3, fibrinogen, and IgG in both RA patients (FIG. 4A,B).

RA synovial tissue was minced and the protein contents extracted with tissue protein extraction buffer. Lysates were immunoprecipitated with protein-G-sepharose to capture immune complexes present in the rheumatoid synovial tissue. These immune complexes were eluted from the protein-G beads, trypsinized, and the trypsin digests directly analyzed by mass spectroscopy to demonstrate the presence of citrullinated fibrinogen in immune complexes isolated from RA pannus tissue (FIG. 4C). These data suggest that citrullinated-fibrinogen containing ICs either deposit or form in synovial tissue in RA. The co-localization of citrullinated fibrinogen-containing immune complexes with complement component C3 in RA pannus further suggests that they could activate the complement cascade to cause synovitis in RA.

The presence of ICs in the blood and inflamed joints of patients with RA has been described. Although ICs have been isolated from RA patient plasma by means of polyethylene glycol precipitation and C1q affinity columns, the identity of the antigens incorporated in these ICs is not well defined. We characterize herein circulating and synovial tissue ICs, and demonstrate the presence of circulating ICs containing fibrinogen in one-half of CCP+RA patients (FIG. 1). We utilize immunoblotting and mass spectroscopy to demonstrate that the fibrinogen contained in these circulating ICs is citrullinated (FIG. 2B,C), and that ICs isolated from RA pannus tissue also contain citrullinated fibrinogen (FIG. 4C). Finally, we demonstrate co-localization of complement component C3, fibrinogen and Ig in RA pannus tissue (FIG. 4A,B), showing that these complexes contribute to synovitis in RA.

Fibrinogen-containing immune complexes were not observed in plasma derived from patients with a variety of other inflammatory arthritidies for which the plasma was collected and stored alongside the CCP+ RA plasma in which fibrinogen immune complexes were demonstrated (FIG. 1C,D). Although complement containing immune complexes usually bind to erythrocytes and are transported to the liver for clearance, we found circulating C1q bound ICs that contain fibrinogen in plasma derived from CCP+ RA patients. Further, fibrinogen ICs were also detected by anti-C1q monoclonal antibody capture, and results were concordant with our results from C1q capture of ICs (comparison of results yielded a $R^2$ value of 0.9 in linear regression).

There is growing evidence that fibrin is an important autoantigen in RA. Autoantibody reactivity was only observed against citrullinated fibrinogen, and not against its native form. Although the anti-citrullinated fibrinogen antibodies observed in RA do not result in overt clinical hematologic manifestations, RA is characterized by extravascular coagulation and the accumulation of fibrin in the arthritic joint. Autoantibodies targeting citrullinated fibrinogen could contribute to a local imbalance between coagulation and fibrinolysis by altering the structural and/or functional properties of fibrinogen and/or fibrin.

Figure 2:
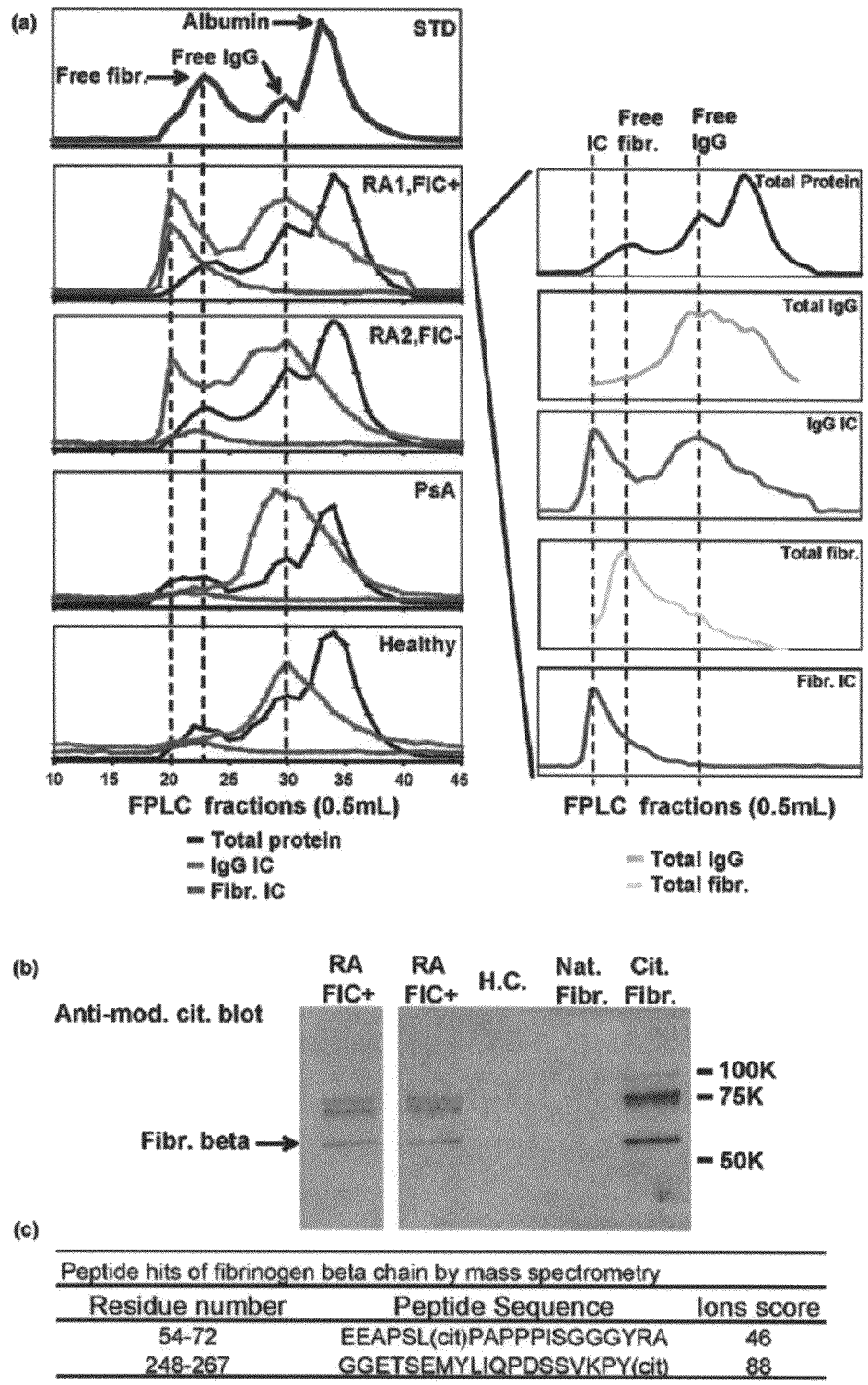
FIG. 2. Citrullinated fibrinogen-containing ICs are separated from RA plasma. A, Liquid chromatographic separation of RA plasma. Fast protein liquid chromatography (FPLC) was used to fractionate plasma derived from RA and control patients. Forty-five fractions were collected from each plasma sample, and individual fractions were analyzed for total protein, fibrinogen, IgG, IgG ICs, and fibrinogen ICs, and relative levels of each of these components are plotted. Plasma samples from two RA patients (RA1 and RA2), a psoriatic arthritis patient (PsA) and a healthy control were characterized. The right panel presents individual traces from patient RA1, with the dashed lines indicating the fractions containing the peak levels of ICs, free fibrinogen, and free Ig. B, Citrullinated fibrinogen was identified by anti-modified citrulline blot. C, In-gel trypsin digestion of the bands followed by mass spectrometry revealed two citrullinated peptides derived from beta chain of human fibrinogen.

Fibrin is one of the classical citrulline-modified proteins. Citrullinated fibrinogen is generated in inflamed synovia arising from a variety of inflammatory conditions. Our observation that ICs containing citrullinated fibrinogen are present in the plasma of CCP+ RA patients, but not in plasma derived from CCP− RA, CCP− JRA, and psoriatic arthritis patients (FIG. 1, 2), suggests a unique potential role for citrullinated-fibrinogen containing circulating ICs in RA. Our mass spectrometry analysis of the fibrinogen contained in CICs derived from CCP+ RA patients demonstrated a few citrullinated peptides from the alpha chain of fibrinogen. Our results are consistent with citrullinated epitopes derived from the beta, but not the alpha, chain of fibrinogen. Although trypsin has been described to be incapable of cleaving C-terminal to citrulline residues, two of the three citrullinated peptides identified contain a citrulline at the C-terminus (FIGS. 2C and 4C). Using mass spectrometry analysis, we have detected multiple citrullinated peptides with C-terminal citrullines (as well as non-C terminal citrullines) in tryspin digests of multiple different citrullinated proteins in multiple experiments. In addition, citrullinated peptides with C-terminal citrullines were also observed from multiple citrullinated proteins that were sent to and analyzed by an independent mass spectrometry core facility. The highly significant Mascot scores of our reported citrullinated peptides (FIGS. 2C and 4C) support the validity of our results.

The excessive formation of fibrin in the rheumatoid joint in combination with its citrullination and structural properties that include repetitive antigenic motifs, may result in activation of B cells specific for citrullinated fibrinogen via crosslinking of surface immunoglobulin receptors.

Our results show that development of autoantibodies targeting citrullinated epitopes specific to fibrinogen play an important role in the pathogenesis of RA. It was unexpected to observe autoantibodies targeting citrullinated fibrinogen along with fibrinogen-containing circulating ICs in a subset of JRA patients (FIG. 1, Table 2). However, late onset polyarticular JRA is associated with RF-positivity in about 5% of patients, and has been considered to be identical to adult RA. Following the observation of anti-citrullinated fibrinogen autoatibodies and fibrinogen-containing circulating ICs in a subset of JRA (Table 2), we performed chart reviews along with CCP and RF ELISA tests on these plasma samples. Of the 6 JRA patients exhibiting elevated levels of anti-citrullinated fibrinogen antibodies, all exhibited a symmetrical polyarthritis and possessed rheumatoid factor antibodies. All but one of the 6 CCP+ and RF+ JRA patients possessed high levels of fibrinogen immune complexes. The age of disease-onset of the CCP+ and RF+ JRA patients were 13, 11, 3, 13 and 9 years, and these patients were relatively older than the other JRA patients included in this cohort. Interestingly, 5 out of 6 CCP+ and RF+ JRA patients possessed fibrinogen-containing ICs, compared to only 50% of CCP+ and RF+ adult RA patients. This observation suggests that anti-fibrinogen autoimmunity and fibrinogen containing ICs play a significant role in this subset of JRA patients and contributes to synovitis in RA.

TABLE 2

Clinical and laboratory characteristics of the JRA patients characterized.

| Sample | Clinical features and rheumatoid factor status | Age Onset | Age Dx | Fibrinogen ICs (O.D.) | Anti-cit. fibrinogen IgG (O.D.) | CCP[a] (IU/mL) | RF[b] (IU/mL) |
|---|---|---|---|---|---|---|---|
| JRA 1 | Polyarthritis, RF− | 2 | 2 | 0.18 | 0.11 | 21.3 | 11.7 |
| JRA 4 | Polyarthritis, RF+ | 13 | | 0.77 | 1.25 | 841.1 | 127.6 |
| JRA 8 | Polyarthritis, RF+ | 3 | 16 | 0.53 | 0.43 | 483.2 | 262.6 |
| JRA 13 | Polyarthritis, RF+ | 13 | 13 | 0.54 | 1.45 | 255.4 | 274.7 |
| JRA 17 | Systemic Arthritis | | | 0.15 | 0.10 | 24.8 | 24.9 |
| JRA 22 | Polyarthritis, RF− | 15 | 15 | 0.13 | 0.09 | 22.7 | 27.1 |
| JRA 27 | Polyarthritis, RF− | 1 | 2 | 0.10 | 0.08 | 20.3 | 7.6 |
| JRA 31 | Persistent Oligoarthritis | | | 0.16 | 0.13 | 21.5 | 7.3 |
| JRA 32 | Polyarthritis, RF− | 5 | 5 | 0.12 | 0.37 | 26.7 | 6.3 |
| JRA 41 | Enthesitis Related Arthritis | 13 | 14 | 0.14 | 0.08 | 20.8 | 13.1 |
| JRA 42 | Systemic Arthritis | 12 | 12 | 0.17 | 0.08 | 21.8 | 7.1 |
| JRA 44 | Polyarthritis, RF− | 9 | 9 | 0.19 | 0.09 | 20.9 | 10.1 |
| JRA 49 | Polyarthritis, RF+ | 9 | | 1.72 | 0.74 | 1275.4 | 295.2 |
| JRA 51 | Systemic Arthritis | 5 | 5 | 0.14 | 0.09 | 21.4 | 7.6 |
| JRA 71 | Polyarthritis, RF+ | | 10 | 0.19 | 0.21 | 360.9 | 186.1 |
| JRA 79 | Polyarthritis, RF− | 4 | 4 | 0.20 | 0.10 | 22.1 | 11.7 |
| JRA 88 | Polyarthritis, RF+ | 11 | 11 | 0.51 | 0.35 | 287.0 | 236.4 |
| JRA 106 | Extended Oligoarthritis | 1 | 3 | 0.15 | 0.12 | 22.0 | 10.0 |
| JRA 110 | Persistent Oligoarthritis | | | 0.15 | 0.10 | 24.9 | 14.6 |
| JRA 112 | Enthesitis Related Arthritis | | | 0.14 | 0.12 | 22.5 | 15.9 |

[a,b]measured with commercial kits.
The highlighted patients are JRA patients with clinical polyarthritis and positive laboratory tests for fibrinogen ICs, anti-citrullinated fibrinogen antibodies, anti-CCP antibodies, and rheumatoid factor.
JRA = juvenile rheumatoid arthriti;
IC= immune complex;
CCP = cyclic-citrullinated peptides;
RF = rheumatoid factor.

Figure 4:
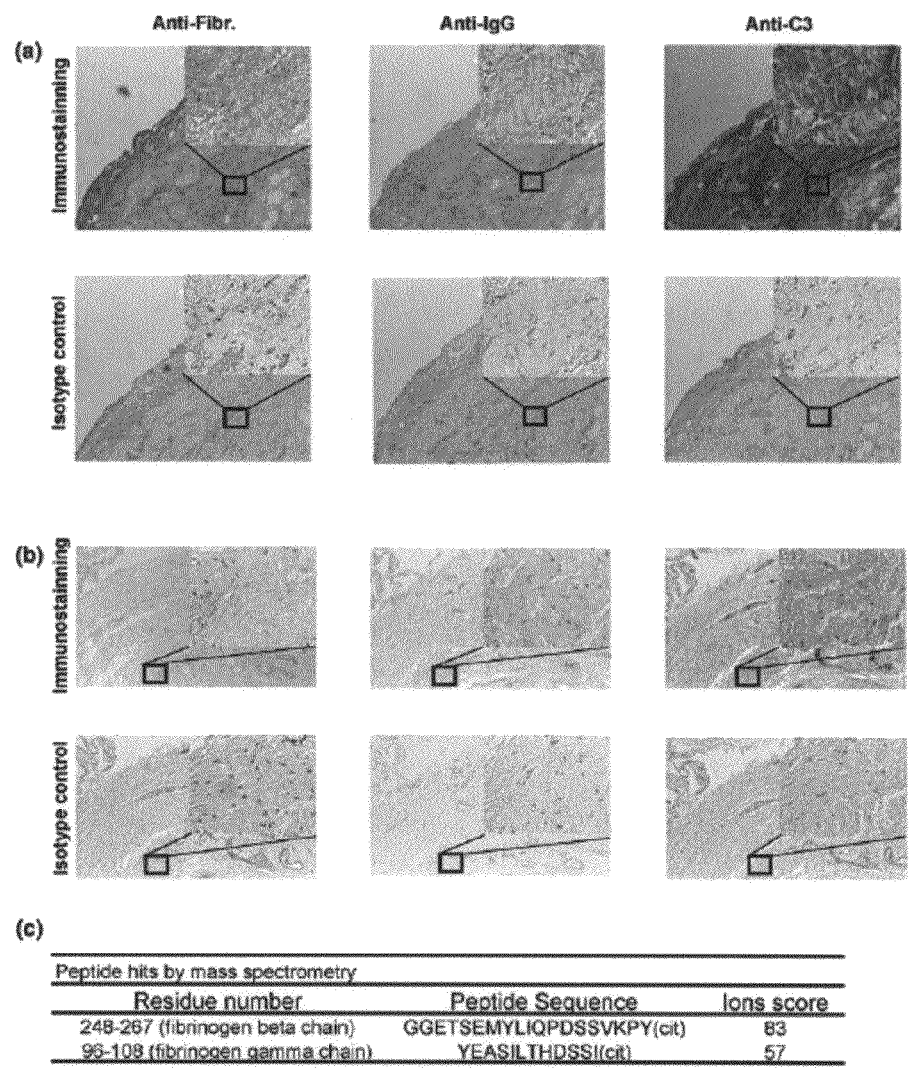
FIG. 4. Synovial tissue immune complexes contain citrullinated fibrinogen. A-B, Immunohistochemistry demonstrates co-localization of fibrinogen, complement component C3 and Ig in RA pannus tissue. Representative staining of synovium derived from two separate CCP+ RF+ RA patients are shown in A and B. Immunohistochemistry was performed on articular cartilage samples derived from RA patients. Samples were fixed, paraffin-embedded, and sections stained with antisera specific for complement component C3, fibrinogen and IgG, as well as with matched pre-immune sera. HRP-conjugated secondary antibodies were utilized to detect primary antibody reactivity. These stainings demonstrate co-localization of complement component C3, fibrinogen and Ig staining at the surface of the articular cartilage sections. C, Mass spectrometry analysis of ICs immunoprecipitated from RA synovial tissue demonstrates the presence of citrullinated fibrinogen peptides.

Immunohistochemical analysis demonstrated co-localization of the staining for fibrinogen, complement component C3 and Ig in serial sections derived from RA pannus tissue (FIG. 4). These results suggest that fibrinogen-containing ICs deposit on or form in synovial lining tissue, and activate the complement cascade to cause inflammatory arthritis. In the K/BxN model, arthritis is mediated by anti-GPI antibodies and was demonstrated to depend on FcRγ and components of the alternative complement pathway. Autoantibodies targeting citrullinated fibrinogen could result in IC-mediated arthritis based on mechanisms analogous to those observed in the K/BxN model and via macrophage FcγRIIa-mediated TNF production.

Anti-citrullinated fibrinogen autoantibodies were detected in three-quarters while fibrinogen containing immune complex were found in one-half of CCP+ RA patients (FIGS. 1 and 3). These observations are consistent with RA being a clinically and molecularly heterogeneous disease, as evidence by differential expression of anti-citrulline antibodies, variable responsiveness to anti-TNF therapy, and heterogeneity in the genetic background of patients which includes polymorphisms in the MHC, TRAF1-C5, STAT4 and PTPN22 genes. CCP is derived from filaggrin, a protein expressed by keratinocytes in the epidermis, and it is likely that autoantibody reactivity against the cyclic citrullinated peptides (CCPs) derived from filaggrin represents molecular cross reactivity. Our findings show that the development of citrullinated fibrinogen-containing ICs in RA synovial tissue activates the complement cascade.

Example 2

Autoimmunity Against Fibrinogen Mediates Inflammatory Arthritis in Mice

Mice with type II collagen (CII)-induced arthritis (CIA) develop antibodies against both CCPs and in vitro citrullinated fibrinogen, and transfer of an anti-citrullinated fibrinogen monoclonal antibody worsened the mild arthritis induced by anti-CII antibody transfer. These findings indicate that antibodies against citrullinated fibrinogen can exacerbate arthritis induced by a distinct autoantigen. To investigate a role for fibrinogen as a central autoantigen in the pathogenesis of RA, we developed a fibrinogen-induced arthritis (FIA) mouse model using human fibrinogen, which naturally contains several citrulline modifications, as the immunizing antigen. Our data show that FIA is a T-cell and autoantibody-mediated autoimmune synovitis that is highly representative of the subset of RA patients that possess anti-citrullinated fibrinogen autoantibodies.

Materials and Methods

Mice. Male DBA1/J mice and female SJL/J, BALB/c, and C57BL/6 mice were obtained from Jackson Laboratories (Bar Harbor, Me.) and were between 7 and 9 weeks of age when experiments were initiated. Adoptive transfer recipients were between 5 and 7 weeks of age. All animal protocols were approved by the Committee of Animal Research at Stanford University, in accordance with the National Institutes of Health guidelines.

Arthritis Induction

FIA induction: mice were immunized subcutaneously with 0.2 mg human fibrinogen (which contains citrulline modifications) (Sigma, St. Louis, Mo. or Calbiochem, Gibbstown, N.J.) in PBS (without calcium or magnesium) emulsified with an equal volume of complete Freund's adjuvant (CFA) consisting of incomplete Freund's adjuvant (IFA, Sigma, St. Louis, Mo.) and 0.5 mg heat-inactivated *Mycobacterium tuberculosis* (strain H37 RA; Difco Laboratories, Detroit, Mich.). Twenty-one days later, the mice were boosted subcutaneously with a second injection of human fibrinogen in IFA.

CIA induction: mice were immunized intradermally at the tail base with 0.2 mg bovine type II Collagen (CII) in 0.05 M acetic acid (immunization grade, Chondrex, Redmond, Wash.) emulsified with an equal volume of CFA. Twenty-one days later, the mice were boosted subcutaneously at the base of the tail with a second injection of bovine CII in IFA.

FIA-CIA induction: mice were immunized subcutaneously to induce FIA and intradermally to induce CIA, as described above, and boosted 21 days later with fibrinogen emulsified in IFA as described above. Control mice were given the equivalent amount of CFA and IFA at the corresponding sites of injection.

Adoptive transfer of FIA: for T-cell transfer, whole splenocytes and lymphocytes from mice with FIA were cultured in vitro for 72 h with 0.01 mg/ml fibrinogen. Cells were harvested and washed with PBS. CD3+ T cells were isolated using CD3+ T-cell enrichment columns (R&D systems, Minneapolis, Minn.). 50 million T cells were injected intravenously into naïve recipients. For plasma transfer, 0.3 ml of pooled plasma from mice with FIA was injected intravenously on days 0 and 2 into naïve recipients.

Animals were scored every 2-3 days for arthritis by using the following scale: grade 0, no erythema or swelling; grade 1, erythema and mild swelling extending from the ankle to the mid paw; grade 2, erythema and moderate swelling extending from the ankle to the metatarsal joint; grade 3, erythema and severe swelling encompassing the ankle, paw and digits. Each paw was graded and the four scores totaled such that the maximal possible score per mouse was 12.

Proliferation Assay. $5\times10^5$ bulk splenocytes were cultured in 96-well microtiter plates and stimulated with 0.01 mg/ml human fibrinogen in triplicate wells for 72 h. Enriched tissue culture media consisted of RPMI 1640 supplemented with HEPES buffer (25 mM), L-glutamine (2 mM), sodium pyruvate (1 mM), nonessential amino acids (0.1 mM), penicillin (100 U/ml), streptomycin (0.1 mg/ml), 2-mercaptoethanol ($5\times10^{-5}$ M), and 10% fetal bovine serum. Cells were pulsed with 1 µCi[$^3$H]TdR (GE Healthcare Bio-Sciences, Piscataway, N.J.) for the final 16 h of culture, and incorporated radioactivity measured by using a betaplate scintillation counter.

Cytokine Analysis. Bulk splenocytes were incubated in enriched RPMI-1640 and 0.01 mg/ml human fibrinogen. After 72 h of culture, the supernatants were collected and assayed in triplicate for levels of IL-6, IL-17, IFN-γ and TNF-α by using commercial ELISA kits (BD PharMingen, San Diego, Calif. and eBioscience, San Diego, Calif.).

Antibody Detection. The levels of autoantibodies to fibrinogen or in vitro citrullinated fibrinogen were determined by ELISA. In brief, ELISA plates (Nunc, Maxisorp, VWR) were coated with 0.01 mg/ml fibrinogen or in vitro citrullinated fibrinogen in 1× phosphate buffered saline (PBS, no calcium or magnesium) overnight at 4° C. Plates were blocked with PBS, 0.05% Tween-20, and 3% fetal bovine serum for 1 h at room temperature. Plasma samples were diluted 1:100 and incubated in duplicate wells for 2 h at room temperature. Horseradish peroxidase (HRP)-conjugated goat anti-mouse secondary antibodies specific for IgG, IgG1, and IgG2a (Southern Biotechnology Associates, Birmingham, Ala.) were diluted 1:5000 and incubated for 1 h at room temperature. TMB substrate was added for 30 min and optical density (OD) values determined at 450 nm. Average absorbance from blank wells (no plasma added) was subtracted.

Detection of Immune Complexes, anti-CCP antibodies, and RF. ELISA plates were coated with 0.02 mg/mL C1q (Sigma) in PBS overnight at 4° C. Subsequent incubations and washes were done at room temperature. The plates were blocked with PBS, 0.05% Tween-20, and 3% BSA for 1 h. After washing, plasma from immunized or naïve mice were diluted 1:50 and incubated on a shaker for 1.5 h. ICs were detected with HRP-conjugated rabbit antiserum specific for mouse IgG (Jackson Immunoresearch Laboratories, Inc., West Grove, Pa.).

Quanta Lite CCP3 IgG ELISA (INOVA Diagnostics, San Diego, Calif.) and Mouse RF immunoglobulins (total IgG) ELISA (Alpha Diagnostic International, San Antonio, Tex.) were performed according to the manufacturer's protocol (plasma diluted 1:100) except that the secondary antibodies used were HRP-conjugated goat anti-mouse secondary antibodies specific for IgG (H+L), IgG1, and IgG2a (1:5,000 dilution, Jackson ImmunoResearch Laboratories, West Grove, Pa. and Southern Biotechnology Associates, Birmingham, Ala.). Anti-CCP antibody values were expressed as concentration units, and RF values were expressed as optical density (OD). Samples were run in duplicate and averaged.

Mass spectrometry analysis. Proteins were treated with trypsin overnight at 37° C. The tryptic peptides were resolved by HPLC by using a Zorbax 300SB-C18 nanocolumn (Agilent Technologies) and eluted at 300 nL/min with a 60-min linear gradient from 0 to 95% acetonitrile containing 0.1% formic acid. Separated peptides were electrosprayed into an ion trap mass spectrometer (XCT Plus, Agilent Technologies). Peptides were identified by using Mascot (Matrix Science) to compare raw MS/MS data with a SwissProt database.

Antigen Array Analysis. Synovial antigen arrays and the associated methods used in this work were previously described in detail. The 1536-feature synovial antigen arrays contain 225 antigens including proteins and overlapping peptides representing candidate autoantigens relevant to RA. The antigen arrays were produced by using a robotic microarrayer to attach peptides and proteins to Arraylt SuperEpoxy microscope slides (TeleChem International, Sunnyvale, Calif.). Arrays were probed with 1:200 dilutions of plasma from individual mice. Reactive antibodies were detected using Cy3-conjugated goat anti-human or goat-anti-mouse IgG/IgM secondary antibody (1:4,000 dilution, Jackson Immunoresearch) prior to scanning. GenePix Pro 5.0 software (Axon Instruments) was used to determine the net median pixel intensities for each antigen feature. Data analysis was performed using Significance Analysis for Microarrays (SAM) software to identify antigen features with statistically significant differences in reactivities between the experimental groups. Cluster software was then used to hierarchically group the samples and antigen features on the basis of a pairwise similarity function, and TreeView software was used to display the data as a heat map. Pathology. Mice were euthanized and both hind limbs dissected, formalin-fixed and decalcified. The samples were embedded in paraffin, sectioned, and stained with hematoxylin and eosin (H&E) or toluidine blue (Premier Laboratory, LLC, Boulder, Colo.) according to standard procedures. Representative sections are shown at 4× and 20× magnifications. Sections were evaluated by a blinded investigator for synovitis, pannus, and bone and/or cartilage destruction on the basis of a previously described scoring system: grade 0=normal; grade 1=mild inflammation, mild hyperplasia of the synovial lining layer, and mild cartilage destruction without bone erosion; grades 2-4=increasing degrees of inflammatory cell infiltrates, synovial lining hyperplasia and pannus formation, and cartilage and bone destruction.

Statistical evaluation. Mann-Whitney U-test was used for statistical evaluation of diseased mice. An unpaired Student's t-test was used for statistical evaluation of groups with unknown and potentially disparate variances.

Results

Figure 5:
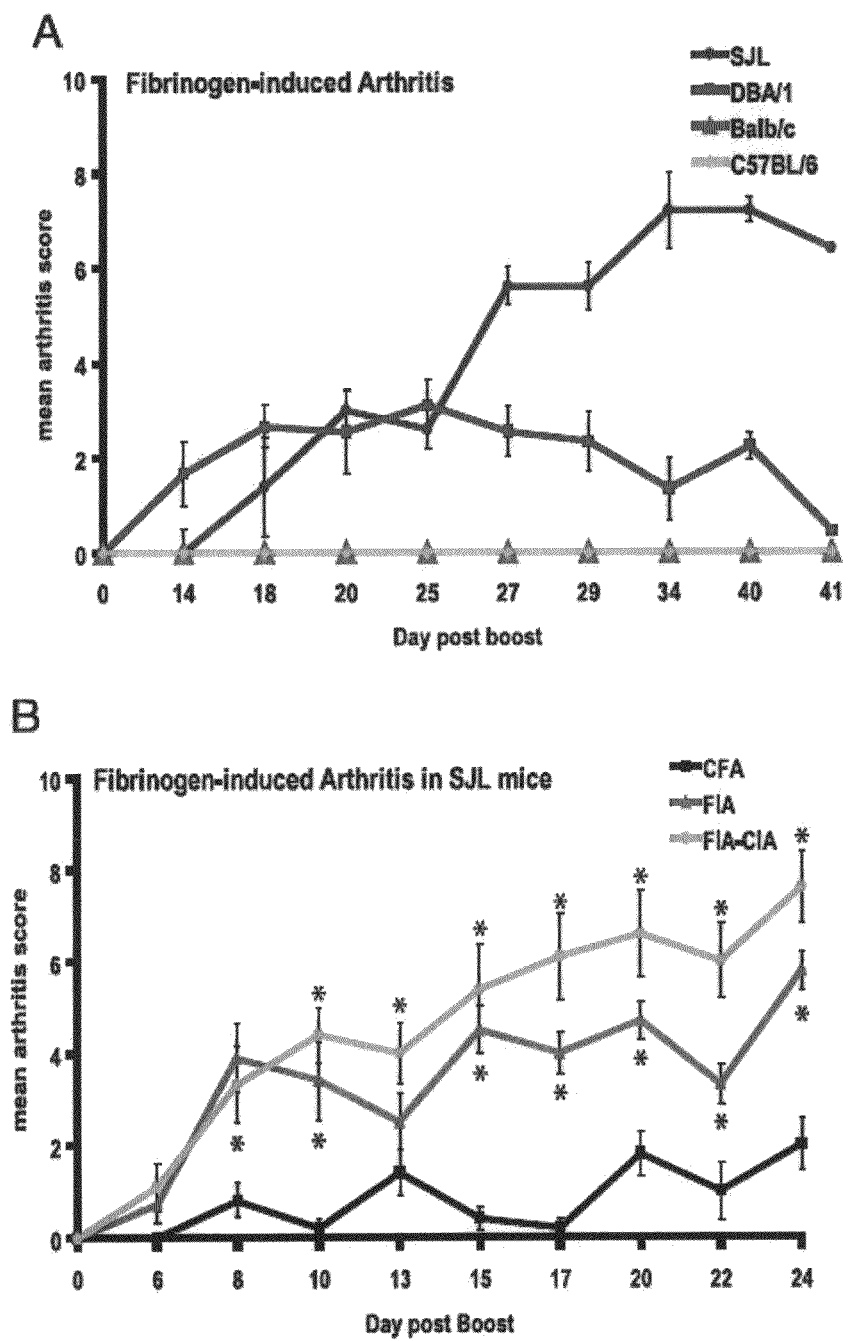
FIG. 5. Immunization with fibrinogen induces arthritis in SJL and DBA/1 mice. (A) SJL (n=5) and DBA/1 (n=5), but not BALB/c (n=3) or C57131/6 (n=3), mice develop inflammatory arthritis following immunization and boosting with human fibrinogen emulsified in CFA. (B) SJL mice immunized to develop FIA (n=10) or a combination of FIA and CIA (n=10) exhibit chronic inflammatory arthritis, whereas mice immunized with CFA alone (n=10) exhibit only minimal signs of arthritis. Data are representative of >5 independent experiments with 5-10 mice per group in each experiment. (C) Splenocytes isolated from mice with FIA were stimulated with human fibrinogen (0.01 mg/ml), and after 72 hours proliferative responses were quantitated by $^3$H-thymidine incorporation. Stimulation with human fibrinogen induced robust proliferative responses in splenocytes isolated from mice with FIA but not in splenocytes from naïve or CFA-immunized mice. (D) Fibrinogen-stimulated splenocytes from FIA mice, but not from naïve or CFA-immunized mice, produced the proinflammatory cytokines IL-6, TNF-α, IFN-γ, and IL-17. Error bars represent the standard deviation of triplicate measurements.
Figure 5:
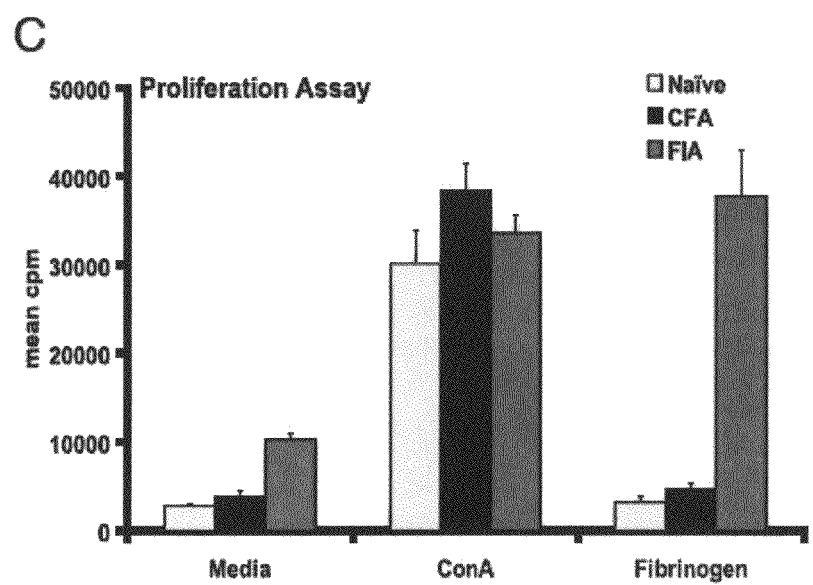
Figure 5:
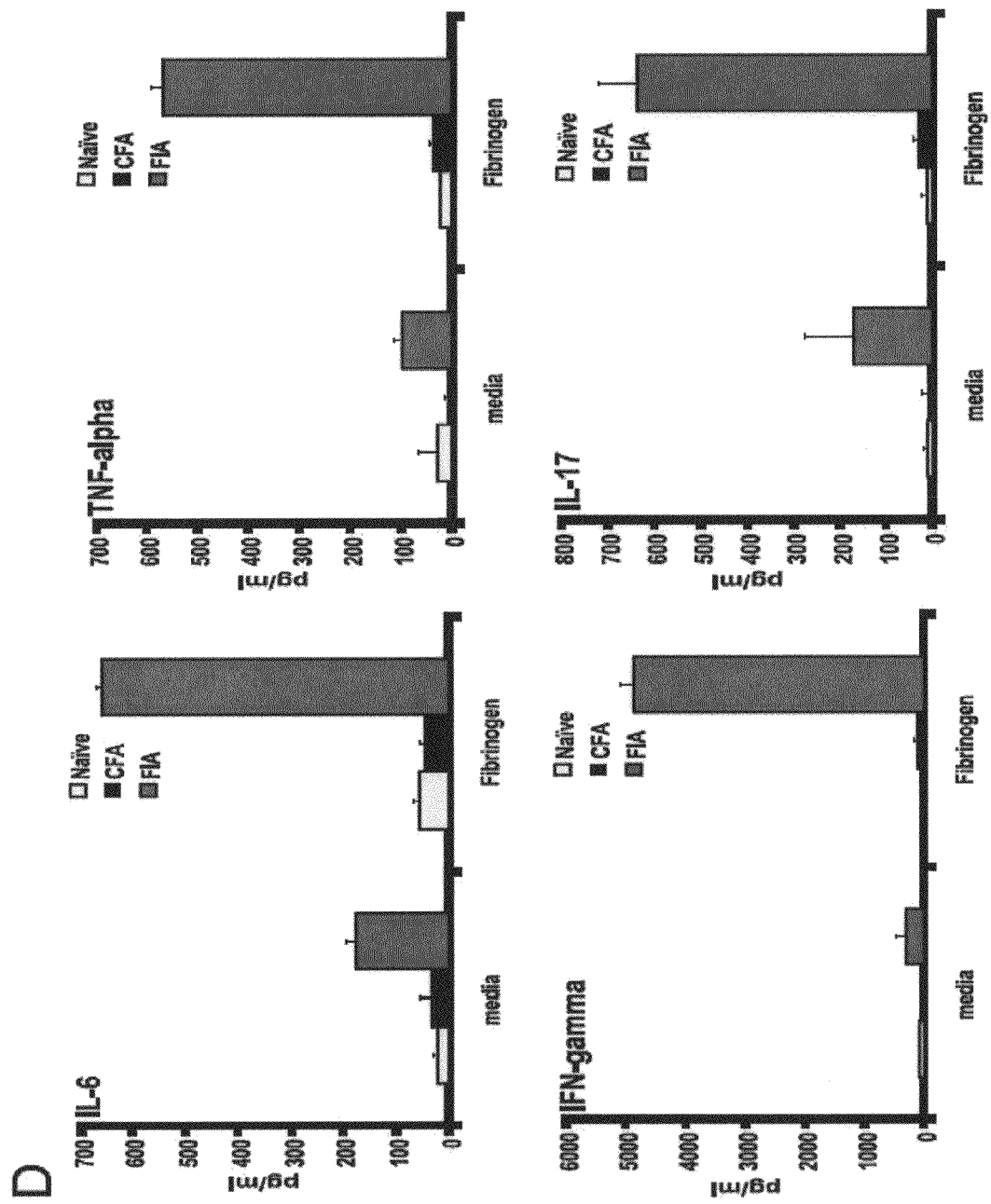

Immunization with human fibrinogen induces an inflammatory arthritis in mice. Because autoantibodies target citrullinated fibrinogen in a subset of anti-CCP antibody-positive (anti-CCP+) RA patients, we sought to determine whether immunization of mice with fibrinogen would induce autoimmune arthritis. We selected a variety of commonly available mouse strains, including C57BL/6, DBA/1, BALB/c, and SJL mice, and immunized them subcutaneously with human fibrinogen (0.1 mg/mouse) emulsified in complete Freund's adjuvant (CFA). Twenty-one days later, the mice received a subcutaneous boost immunization with human fibrinogen (0.1 mg/mouse) emulsified in incomplete Freund's adjuvant (IFA): Two weeks after boosting, both DBA/1 and SJL mice developed an inflammatory arthritis involving the paw(s) on one or more limbs (FIG. 1A). The incidence of arthritis in most experiments approached 100% (FIG. 5). Mass spectrometry analysis of commercially purified human fibrinogen revealed several citrulline modifications on both the alpha and beta chains of fibrinogen (Table 3). This demonstrates that the fibrinogen purified from human blood, which was used for immunization of mice to induce FIA, is already citrullinated to a certain degree.

TABLE 3

Mass spectrometry identified citrulline modifications in fibrinogen purified from human blood.

| Sequence | ion score | P-value |
|---|---|---|
| Fibrinogen alpha chain (gi: 223918) | | |
| RNPSSAGSWNSGSSGPGSTGN*cit*N | 67 | 0.0058 |
| RMELE*cit*PGGNEITRG | 43 | 0.2800 |
| KGLIDEVNQDFTN*cit*I | 50 | 0.0870 |
| RH*cit*HPDEAAFFDTASTGKT | 63 | 0.0035 |
| Fibrinogen beta chain (gi: 399492) | | |
| K. REEAPSL*cit*PAPPPISGGGYRA | 61 | 0.0230 |
| KGGETSEMYLIQPDSSVKPY*cit*V | 82 | 5.00E-05 |
| RTPCTVSCNIPVVSGKECEEI*cit*K | 69 | 0.0011 |
| REEAPSL*cit*PAPPPISGGGYRA | 46 | 0.1100 |

Figure 6:
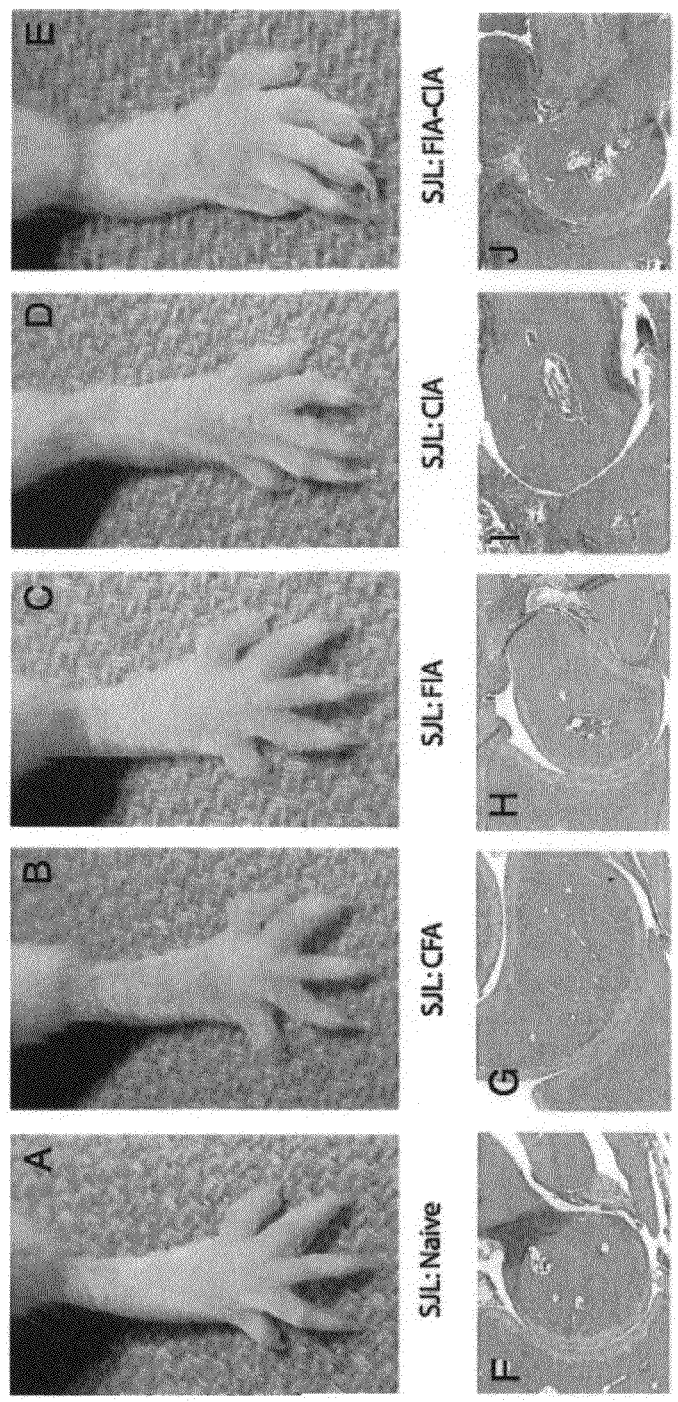
FIG. 6. Fibrinogen-induced arthritis (FIA) involves the digits and mid paw. Images from representative hind paws of naïve mice (A), CFA-immunized mice (B), and mice with FIA (C), CIA (D), or FIA-CIA (E) are presented. Photomicrographs were taken 50 days after the initial disease-inducing immunization and approximately 2 weeks after the development of clinical arthritis in mice with FIA. FIA is characterized by inflammation of the digits and mid paw, with general sparing of the ankles (C), whereas CIA and FIA-CIA are characterized by a fulminant synovitis that involves the whole paw and ankle (F-J). Hind paws harvested 2 weeks after the development of arthritis were embedded in paraffin, sectioned, and stained with HSE. Histopathological analysis demonstrates mononuclear cell infiltration and synoviocyte proliferation suggestive of pannus formation in mice with FIA (H). Paws from mice with CIA and FIA-CIA exhibited intense inflammatory infiltrates, as well as extensive joint destruction and bone erosions. Representative hind paws that were paraffin-embedded, sectioned, and stained with toluidine blue were scored for synovitis (K), pannus (L) and bone erosions (M). Mice with FIA, CIA, and FIA-CIA exhibited significantly more severe synovitis, pannus and erosion than did naïve and CFA-treated mice (P<0.01, unpaired t-test).
Figure 6:
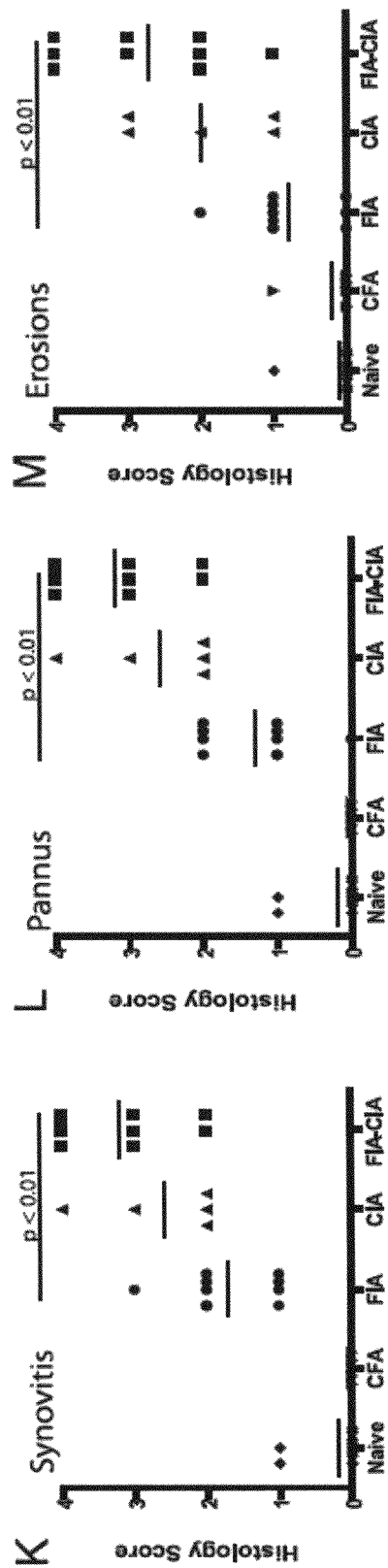

Immunization with fibrinogen resulted in significantly more severe arthritis than did immunization with CFA alone (FIG. 5B, $P<0.05$, by Mann-Whitney). CIA can be induced in SJL mice and is significantly more severe than the mild arthritis associated with CFA immunization. Co-immunization of SJL mice with fibrinogen and type II collagen (FIA-CIA) resulted in arthritis that was more severe than that resulting from immunization with fibrinogen alone ($P<0.05$ on days 22 and 24, by Mann-Whitney). We also observed increased severity in arthritis after co-immunization of DBA/1J mice with fibrinogen and type II collagen (FIA-CIA) as compared to immunization with type II collagen (CIA) alone (FIG. 6).

To determine whether FIA is associated with T-cell responses to fibrinogen, we harvested whole splenocytes from naive mice, mice with FIA, or CFA-immunized mice and cultured the cells in the presence of human fibrinogen (0.01 mg/ml). Splenocytes from mice with FIA proliferated robustly in response to fibrinogen, as measured by [$^3$H]-thymidine incorporation (FIG. 5C). Splenocytes derived from mice with FIA exhibited evidence of basal activation, based on their increased proliferation (FIG. 5C) and cytokine production (FIG. 5D) in the absence of stimulation. We also analyzed the cytokine profiles in the cell culture supernatants from these stimulation assays. Compared to cells derived from naïve and CFA-immunized mice, splenocytes derived from mice with FIA produced high levels of the proinflammatory cytokines IL-6, TNF-α, IFN-γ, and IL-17 in response to fibrinogen (FIG. 5D). Collectively, the data demonstrate that immunization with human fibrinogen containing several citrulline modifications induces autoimmune arthritis in SJL mice, and that diseased mice possess fibrinogen-specific T cells that secrete proinflammatory cytokines.

FIA results in moderate arthritis involving the digits, mid paw and ankle. Images of representative hind paws of naïve mice, CFA-immunized mice, and mice with FIA, CIA, and FIA-CIA show the clinical features of FIA (FIG. 6A-E). The images were taken 50 days following the initial immunization to induce disease, which is 2 weeks following the time at which mice with FIA develop clinical arthritis. CFA immunization induced mild swelling and erythema of the digits and mid paw (FIGS. 6A&B). FIA is characterized by arthritis involving the digits, mid paw and, to a lesser degree, the ankle (FIG. 6C). Mice with CIA (FIG. 6D) and FIA-CIA (FIG. 6E) developed more severe arthritis involving the paw and ankle. Bone erosions were observed in approximately 1 in 5 mice with FIA.

Comparisons of H&E-stained ankle joints between the groups of mice revealed a range of histopathological features. Mice immunized with CFA exhibited minimal mononuclear cell infiltrates in the periarticular tissue (FIGS. 6F&G), whereas mice immunized with fibrinogen (i.e., mice with FIA) exhibited moderate mononuclear cell infiltrates in the periarticular tissue and proliferation of synovial lining cells suggestive of pannus formation (FIG. 6H). Mice with CIA and FIA-CIA exhibited massive mononuclear cell infiltrates and marked pannus formation (FIG. 6I and FIG. 6J, respectively).

To further characterize the differences in disease severity between the groups, we performed histological scoring of synovitis (FIG. 6K), pannus formation (FIG. 6L), and bone erosions (FIG. 6M) in a blinded fashion. Minimal synovitis, pannus formation and bone erosions were evident in both naïve and CFA-immunized mice (histology score 0-1). Mice with FIA exhibited intermediate histological scores for synovitis, pannus formation, and bone erosions, which were significantly higher than the scores for naïve and CFA-treated mice (histology score 1-2; $P<0.01$ by unpaired t-test). Mice with CIA exhibited moderate to severe synovitis, pannus formation, and bone erosions (histology score 2-4; $P<0.01$ comparing CIA mice to naïve and CFA-immunized mice by unpaired t-test). Mice with FIA-CIA had the highest scores for synovitis, pannus formation, and bone erosions (histology score 2-4; $P<0.01$ comparing FIA-CIA mice to naïve and CFA-immunized mice by unpaired t-test).

Together, the clinical and histopathological data indicate that FIA results in a moderate inflammatory arthritis that is less severe than CIA. Mice with FIA-CIA exhibit severe arthritis that is more destructive than CIA.

Figure 7:
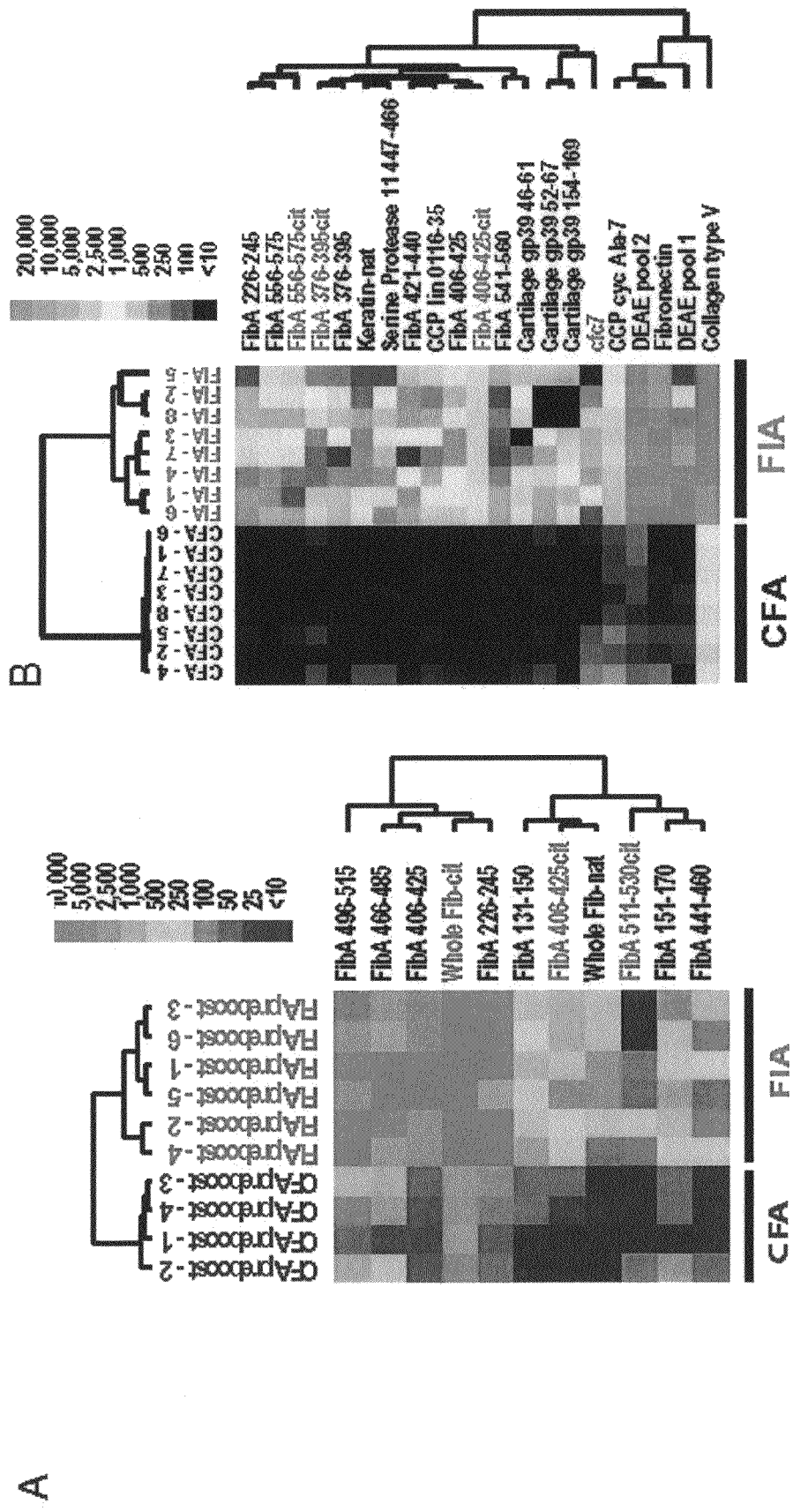
FIG. 7. Mice with FIA develop anti-native and anti-in vitro citrullinated fibrinogen antibodies, anti-CCP antibodies, RF, and immune complexes. (A-B) Synovial antigen arrays were probed with 1:150 dilutions of plasma derived from SJL mice immunized with fibrinogen emulsified in CFA or with CFA alone. Autoantibody binding was detected with a Cy3-conjugated goat-anti-mouse IgG/M secondary antibody. SAM was applied to identify antigens with statistically significant differences in array reactivity between FIA and CFA control plasma (q<0.01) obtained from mice before boosting (A) or 27 days after boosting (B). The SAM hits were subjected to hierarchical cluster analysis and are displayed as a heatmap. Synovial array profiling of FIA plasma demonstrated autoreactive B-cell responses against peptides representing native fibrinogen, and B-cell epitope spreading resulting in additional targeting of citrullinated fibrinogen in the samples obtained before boosting, with further spreading to target CCPs, collagen type V, and cartilage gp39 in samples obtained after boosting. (C) Plasma samples from SJL and DBA/1 mice, immunized as indicated, were diluted 1:100 and assayed for isotype-specific IgG1 and IgG2 antibodies to native and in vitro citrullinated fibrinogen. (D) ELISA was used to measure IgG immune complexes, (E) RF, and (F) IgG anti-CCP antibodies in plasma samples.
Figure 7:
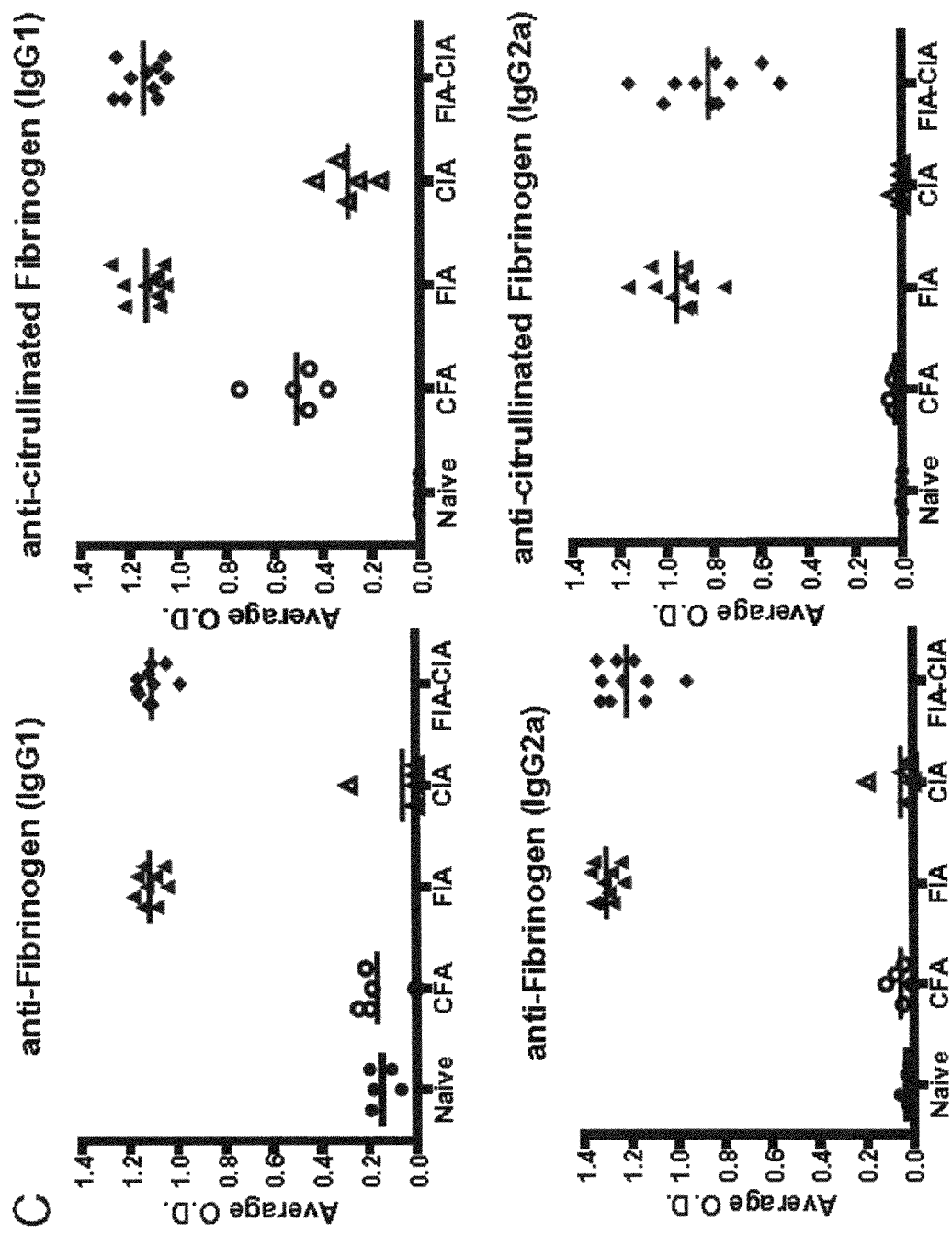
Figure 7:
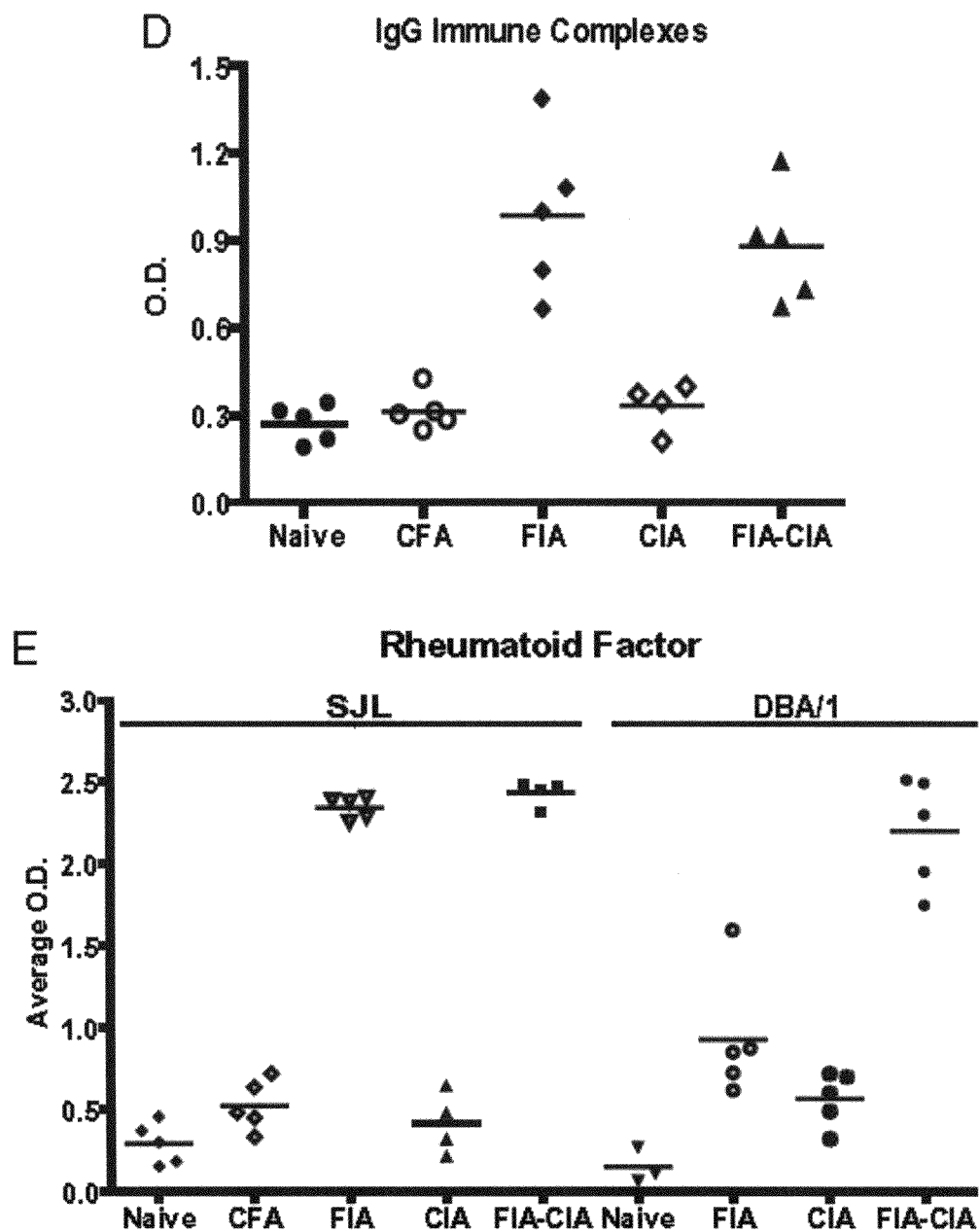
Figure 7:
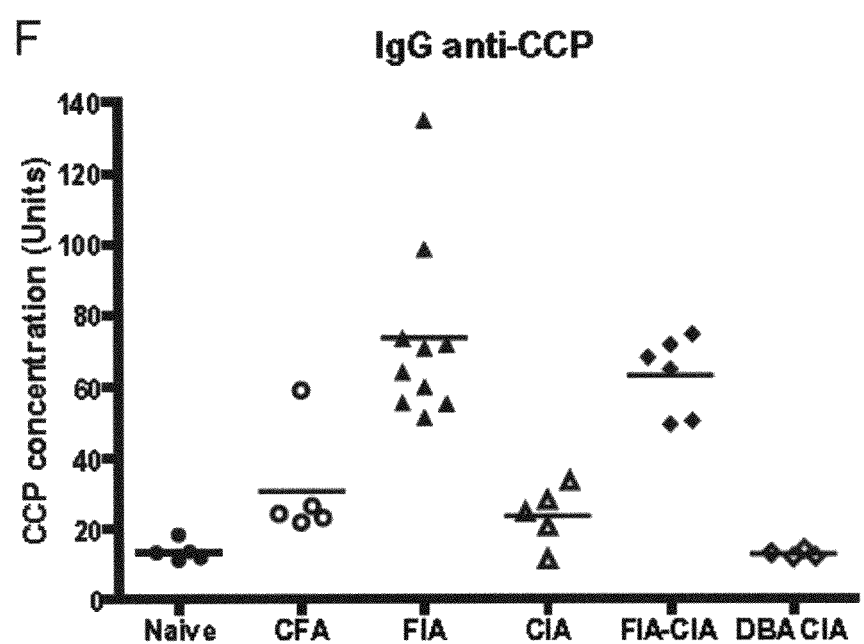

FIA is characterized by autoantibody responses to native fibrinogen that spread to additionally target citrullinated fibrinogen and other synovial autoantigens. We next used arrays containing synovial antigens to profile the IgG/IgM antibodies in the plasma of fibrinogen-immunized and CFA-immunized mice 21 days after the first immunization (i.e., before boosting; FIG. 7A), and 27 days after the second immunization (i.e., after boosting and at the time of arthritis onset; FIG. 7B). SAM analysis of autoantibody reactivity before boosting demonstrated a significant increase in antibody reactivity (false discovery rate ($q$)<0.01) to human "native" fibrinogen protein (fibrinogen purified from human blood which contains several citrulline modifications as demonstrated in Table 3), in vitro citrullinated fibrinogen protein (Whole Fib-cit), as well as unmodified and citrulline-modified fibrinogen peptides, in response to immunization with fibrinogen. CFA-immunized mice exhibited minimal autoantibody reactivity to native fibrinogen protein and moderate reactivity to in vitro citrullinated fibrinogen protein. These data demonstrate that immunization of mice with human fibrinogen induces autoimmunity against both native and citrullinated fibrinogen, and that the autoimmune response to fibrinogen precedes the onset of arthritis.

Synovial array analysis of plasma derived from mice with established FIA (27 days after boosting with fibrinogen emulsified in IFA) demonstrated extensive autoantibody reactivity against unmodified and citrulline-modified peptides derived from fibrinogen. Moreover, plasma from these mice exhibited further spreading of autoantibody responses to target additional candidate RA autoantigens including cartilage gp39 and collagen type V (FIG. 7B). In contrast, plasma from CFA-Immunized mice did not exhibit autoantibody reactivity to these antigens, indicating that FIA is an antigen-driven disease and not simply an adjuvant-induced arthritis. Autoantibody reactivity to fibronectin and the DEAE extraction pools (which also contain fibronectin) in FIA plasma (FIG. 7B) is likely attributable to the binding of fibronectin to the Fc region of Ig in an antigen-independent manner. No antibody reactivity was detected to the vast majority of the 225 candidate antigens on the synovial arrays.

FIA is associated with antibody isotype class switching of anti-fibrinogen and RF B-cell responses. We analyzed plasma derived from SJL mice immunized with CFA and from SJL mice with FIA, CIA and FIA-CIA to determine the IgG antibody isotype(s) of the anti-fibrinogen, anti-CCP and RF responses. In mice with FIA or FIA-CIA, we detected class switching of anti-native fibrinogen B-cell responses to both IgG1 and IgG2a (FIG. 7C, left panels; P<0.01 comparing FIA and FIA-CIA mice to naïve, CFA-treated and CIA-induced mice by unpaired t-test). Of note, IgG1 antibody responses to in vitro citrullinated fibrinogen were found in all groups, with the highest levels observed in mice with FIA and FIA-CIA. In contrast, IgG2a antibody responses to in vitro citrullinated fibrinogen were only observed in mice with FIA or FIA-CIA (FIG. 7C right panels, P<0.01, by unpaired t-test).

A C1q capture assay demonstrated an increase in levels of IgG circulating immune complexes (CICs) in mice with FIA and FIA-CIA (P<0.01, by unpaired t-test) but not in mice with CIA or in CFA-immunized mice (FIG. 7D). An assay for RF revealed highly elevated levels in both SJL and DBA mice with FIA and FIA-CIA compared to mice with CIA and CFA-immunized mice (FIG. 7E, P<0.01, by unpaired t-test).

To determine whether mice with FIA possess IgG anti-CCP antibodies, we performed anti-CCP3 IgG ELISAs on plasma samples. Anti-CCP IgG antibody levels were higher in plasma from mice with FIA compared to plasma from naïve mice (average of 73.4 units from 10 mice, P<0.05, by unpaired t-test). Mice with FIA-CIA also had elevated levels of anti-CCP IgG antibodies in their plasma (average of 63.1 units from 6 mice, P<0.05, by unpaired t-test). Interestingly, compared to DBA1 mice with CIA, SJL mice with CIA developed low but significantly elevated levels of anti-CCP IgG antibodies (average of 23.6 units from 5 mice) (FIG. 7F, P<0.05, by unpaired t-test). CFA immunization of SJL mice was associated with low-level but not statistically significant amounts of anti-CCP IgG antibodies (average of 30.8 units from five mice, P=0.0689, by unpaired t-test).

Figure 8:
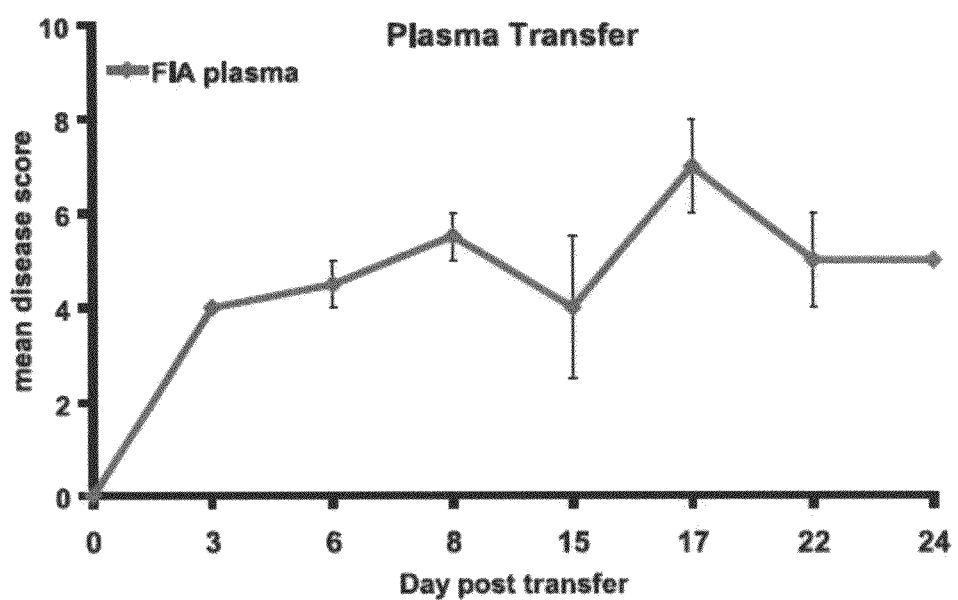
FIG. 8. FIA plasma induces arthritis in naïve mice. Plasma collected from mice with FIA were pooled, and 0.3 ml was injected intravenously into 6-week-old naïve SJL mice on days 0 and 2 (A). Synovial antigen array profiling of plasma from the arthritic recipient mice demonstrated autoreactive B-cell responses against peptides representing native fibrinogen and citrullinated fibrinogen, and further epitope spreading resulting in additional targeting of fibronectin, collagen type V, cartilage gp39, and clusterin (B). Joints from naïve mice that developed arthritis after FIA plasma transfer (without boosting) demonstrated mononuclear cell infiltrates and synoviocyte proliferation (C). Data are representative of three independent experiments with 3-5 mice per group in each experiment. Error bars represent standard error of the mean.
Figure 8:
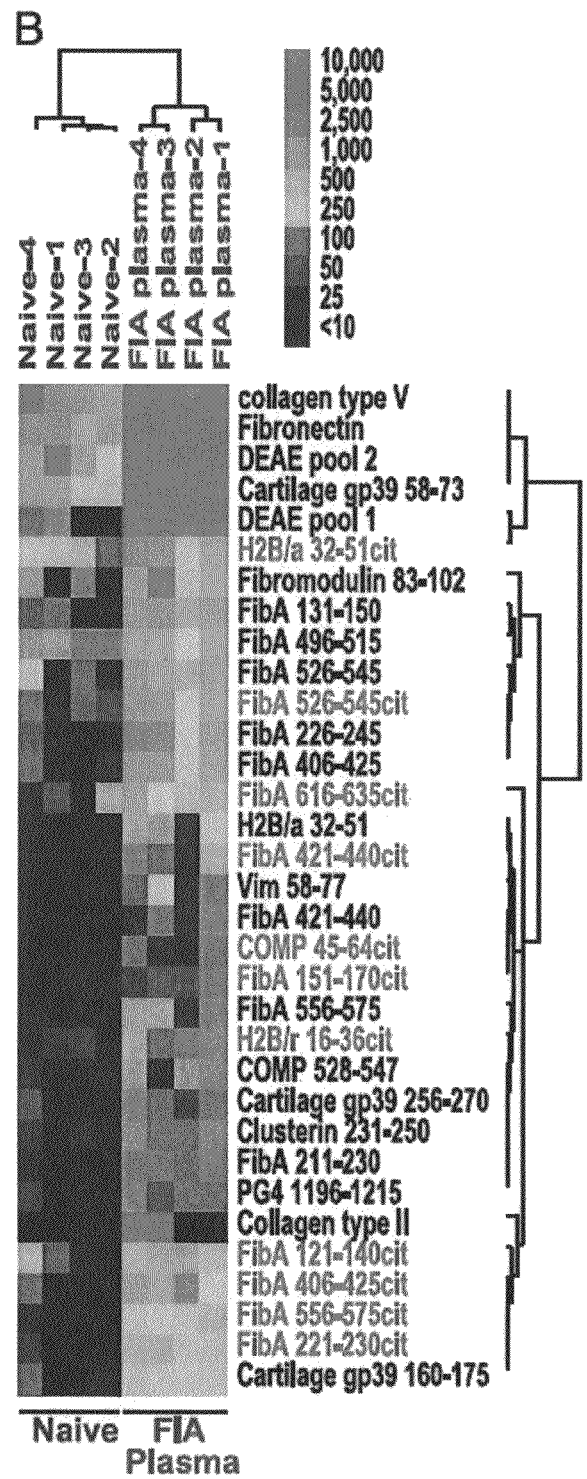
Figure 8:
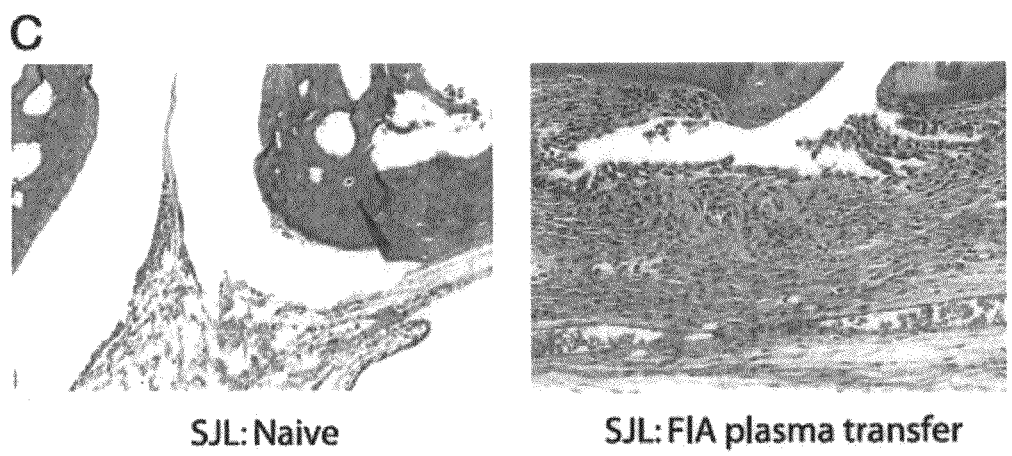

Induction of arthritis by transfer of plasma or fibrinogen-activated T cells from mice with FIA. Plasma from mice with FIA were collected and 0.3 ml of pooled plasma injected intravenously, into naïve SJL mice on days 0 and 2. Three days later, the hind paws of the mice exhibited mild to moderate arthritis, which persisted for 3 weeks (FIG. 8A). Synovial array analysis of FIA plasma demonstrated autoantibody targeting of both native and citrullinated fibrinogen, and of epitopes representing additional candidate autoantigens including collagen type V, cartilage gp39, clusterin and histone 2B (FIG. 8B). H&E staining of joint sections showed infiltration of mononuclear cells and proliferation of synovial lining cells in the ankle joint derived from a representative FIA plasma recipient (FIG. 8C, right panel). No mononuclear cell infiltration or synovial proliferation was observed in the ankle joint derived from a healthy control mouse (FIG. 8C, left panel).

Figure 9:
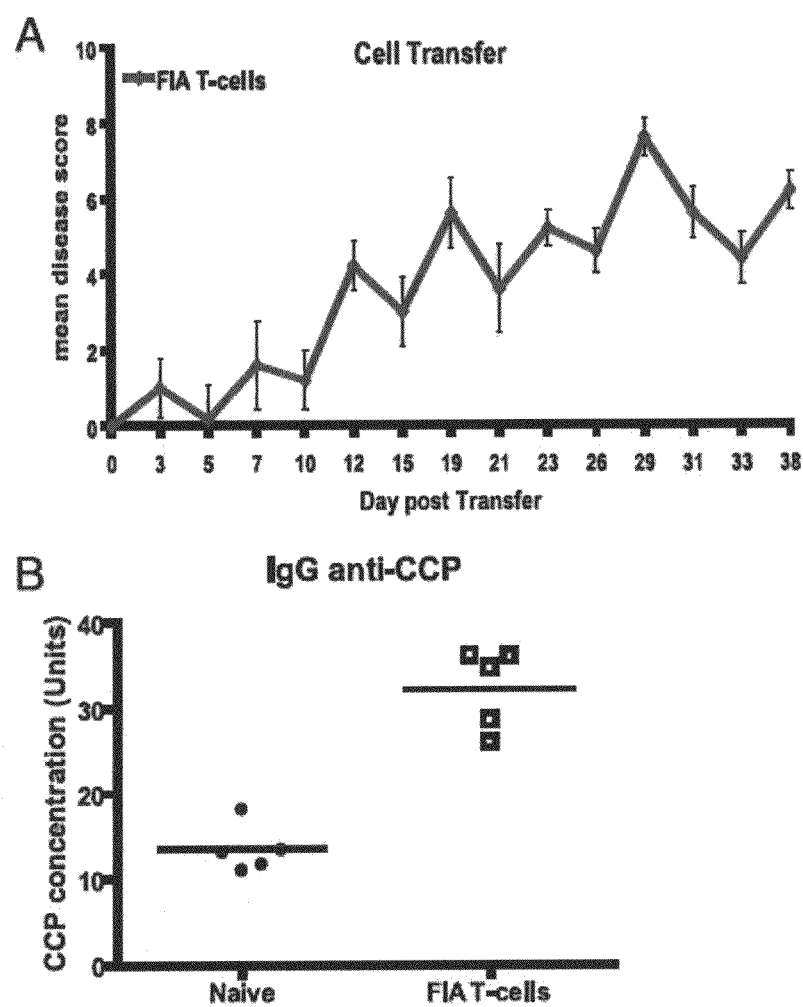
FIG. 9. Fibrinogen-reactive T cells transfer disease to naïve mice. Splenocytes harvested from mice with FIA were cultured in vitro and stimulated with 0.01 mg/ml fibrinogen for 3 days. Enriched T cells were transferred into 6-week-old naïve SJL mice, which developed visible signs of arthritis within 2 weeks (A). Plasma samples taken from the diseased mice 38 days after cell transfer were assayed for IgG anti-CCP antibodies (B). Synovial array profiling of plasma from the arthritic recipient mice demonstrated autoreactive B cell responses against peptides representing native fibrinogen, and further spreading of the responses to target collagen type V, cartilage gp39, and citrullinated vimentin (C). Data are representative of three independent experiments with 3-5 mice per group in each experiment. Error bars represent standard error of the mean.
Figure 9:
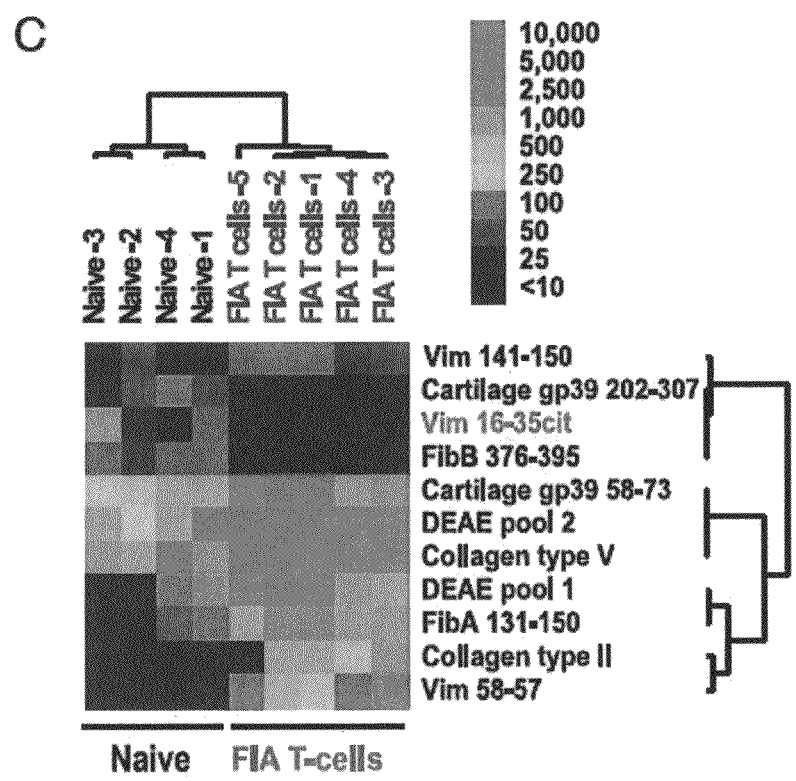

Splenocytes and lymphocytes derived from mice with FIA were co-cultured for 72 hours in the presence of human fibrinogen (0.01 mg/ml). Cultured cells were washed twice and enriched for $CD3^+T$ cells, and $10^8$ cells were injected intravenously into naïve recipient SJL mice (n=8). Within 2 weeks, the recipients exhibited moderate arthritis, which was still evident 38 days after the adoptive transfer, at which time 100% of the mice exhibited clinical arthritis (FIG. 9A). Plasma taken from recipient mice 38 days after the transfer of activated FIA T cells contained significant titers of anti-CCP IgG antibodies (FIG. 9B, average of 32.3 units from five mice, P<0.01, by unpaired t-test). Synovial array analysis of the plasma identified a small set of statistically significant autoantibody reactivities that included reactivity against fibrinogen, vimentin, and collagen type II (FIG. 9C).

Together, these studies demonstrate that the transfer of plasma or fibrinogen-reactive T cells from mice with FIA induces arthritis in naïve recipients, and that plasma and T-cell transfer can induce the production of autoantibodies to CCPs and other candidate RA autoantigens.

Figure 10:
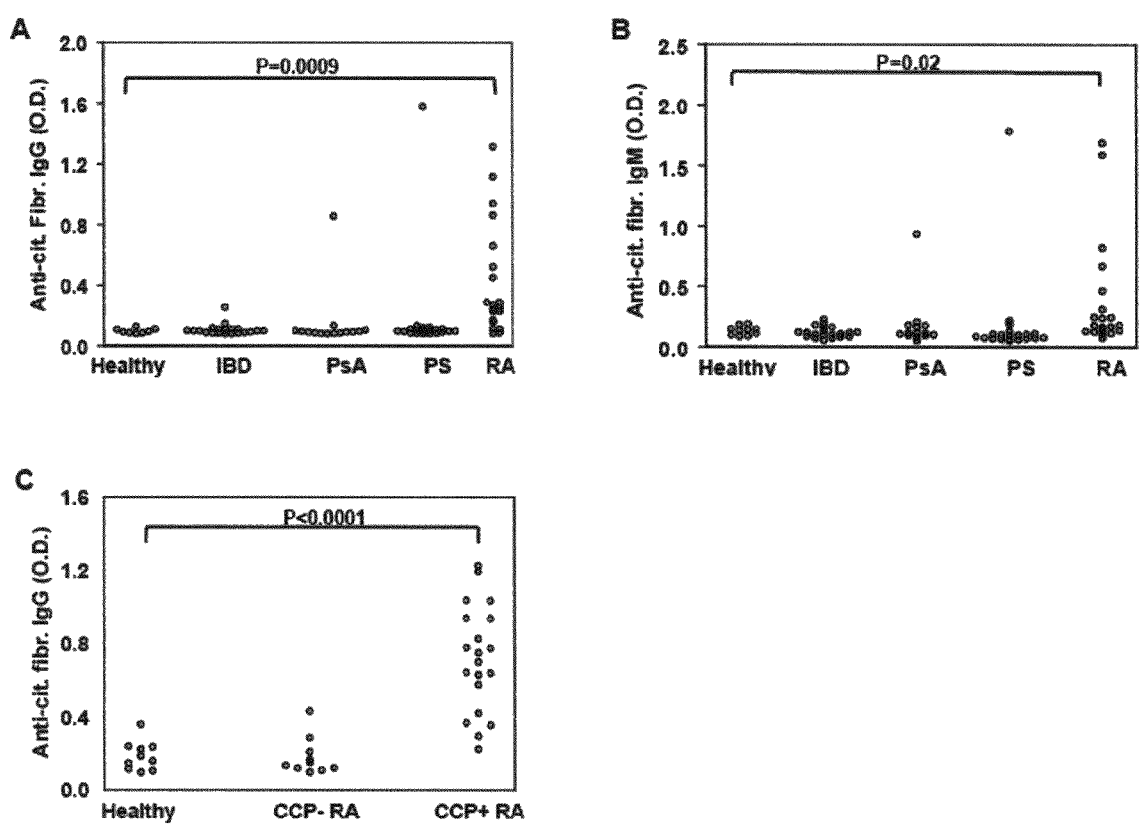
FIG. 10. Anti-CCP-positive RA patients possess antibodies that recognize in vitro citrullinated fibrinogen. IgG (A) and IgM (B) autoantibodies targeting in vitro citrullinated fibrinogen were measured by ELISA in plasma samples derived from healthy individuals (n=10) and patients with inflammatory bowel disease (IBD, n=20), psoriatic arthritis (PsA, n=14), psoriasis (PS, n=20) or RA (n=20). Statistical comparisons were made using an unpaired t-test with Welch correction. (C) Anti-in vitro citrullinated fibrinogen IgG antibodies were measured by ELISA in plasma samples from healthy patients (n=10), anti-CCP antibody-negative RA.

Anti-CCP antibody-positive RA is characterized by autoantibodies targeting citrullinated fibrinogen. To further demonstrate the relevance of FIA to human RA, we characterized the autoantibody reactivity against in vitro citrullinated fibrinogen in a cohort of RA and control patients. ELISA plates were coated with in vitro citrullinated fibrinogen, and IgG/IgM-specific secondary antibodies were used to detect anti-fibrinogen antibody reactivity in plasma derived from healthy individuals (n=10) and from patients diagnosed with inflammatory bowel disease (IBD, n=20), psoriatic arthritis (PSA, n=14), psoriasis (PS, n=20) or RA (n=20). A subset of RA patients possessed IgG (FIG. 10A, P=0.0009, by unpaired t-test) and IgM (FIG. 10B, P=0.02, by unpaired t-test) autoantibodies against in vitro citrullinated fibrinogen, while no autoantibody reactivity was detected against native fibrinogen (which contains several citrulline modifications; data not shown). Analysis of a larger set of anti-CCP antibody-negative (anti-CCP−) and anti-CCP antibody-positive (anti-CCP+) RA patients demonstrated that 80% of anti-CCP+ RA patients possessed elevated titers of IgG autoantibodies to in vitro citrullinated fibrinogen (P<0.0001; by unpaired t-test), whereas only 10% of anti-CCP− RA patients exhibited such an elevation in autoantibody titers (FIG. 10C).

In this study, we describe the development and characterization of FIA as a murine model for the study of RA. Importantly, native fibrinogen, that contains several citrulline modifications based on mass spectrometry analysis (Table 3), was capable of inducing inflammatory arthritis. Additionally, the development of inflammatory arthritis following immunization with fibrinogen was associated with the expansion of autoantibody responses to target both native and citrullinated peptides derived from fibrinogen (FIG. 7A,B). Clinical symptoms include swelling and erythema that encompass the digits, mid paw and ankle/wrist. Joint sections from mice with FIA exhibit mononuclear cell infiltrates within the inflamed synovial membrane, pannus formation, and in some instances, bone erosions. FIA in mice is associated with strong T-cell reactivity to fibrinogen and production of the proinflammatory cytokines IL-6, TNF-α, IFN-γ, and IL-17. Using synovial antigen microarrays, we demonstrated that immunization with fibrinogen induces strong B-cell reactivity to both native fibrinogen, which contains several citrulline modifications, and in vitro citrullinated fibrinogen before the onset of clinical arthritis, with autoantibody responses expanding to include targeting of other candidate RA autoantigens in established FIA. We also show that arthritis can be adoptively transferred to naïve mice with either plasma or fibrinogen-reactive T cells derived from mice with FIA.

Importantly, mice with FIA possess elevated levels of RF, CICs, and anti-CCP antibodies. Detection of RF and anti-CCP antibodies is frequently used in the diagnosis of RA. RF, although associated with more active disease and with the development of bone erosions, is not specific for RA. ACPAs, on the other hand, are highly specific for RA and are also associated with the development of more severe joint destruction. We recently demonstrated the presence of CICs. containing citrullinated fibrinogen in half of anti-CCP+ RA patients, and found that there is a positive correlation between the presence of these complexes and the presence of anti-in vitro citrullinated fibrinogen autoantibodies. Our observation that both anti-CCP and anti-citrullinated fibrinogen antibody titers are elevated in mice with FIA further suggests that FIA is representative of anti-CCP+ and anti-citrullinated fibrinogen antibody-positive RA.

Synovial antigen array analysis of plasma derived from mice with established FIA demonstrated expansion of the autoantibody response to target additional native and citrullinated fibrinogen epitopes, as well as epitopes derived from synovial antigens including fibronectin, type V collagen, and cartilage gp39. Therefore, we propose that the initial immunization with fibrinogen induces autoantibody responses against native and citrullinated fibrinogen epitopes, and that progression to clinical arthritis is associated with the expansion of autoantibody responses to target additional synovial antigens. Similarly; ACPA responses in RA can pre-date clinical arthritis by years, and there is evidence that such responses evolve over time. Antibodies to several citrullinated proteins, including filaggrin, fibrinogen, vimentin, CII, and α-enolase, are observed in human RA. The expansion of ACPA responses in FIA could contribute to more severe and chronic disease.

Mass spectrometry analysis demonstrated that the fibrinogen purified from human blood and used to induce FIA contains several citrulline modifications (Table 3). Native fibrinogen present in human blood may indeed contain several citrulline modifications; alternatively, it is possible that the process of purifying fibrinogen from human blood results in the citrullination of fibrinogen. Despite the low-level citrullination of fibrinogen purified from human blood, ACPAs derived from RA patients do not react with this native fibrinogen. Not all citrulline modifications render a protein immunoreactive with ACPAs, and CICs containing citrullinated fibrinogen are detected in a subset of RA patients. Therefore, these findings suggest that ACPAs target citrullinated fibrinogen epitopes that are not normally present in fibrinogen in the blood but are generated during inflammation-associated citrullination of fibrinogen in synovial joints. Mononuclear cells that infiltrate the synovium during joint inflammation contain PAD enzymes, and the level of both PAD4 and citrullinated proteins in the joints of mice with CIA correlates with the severity of inflammation. Extracellular proteins such as fibrinogen are the primary targets of PADs in inflamed joints; inflammation-driven generation of additional citrullinated epitopes on fibrinogen may thus elicit an ACPA response and contribute to RA pathogenesis.

Our findings suggest that immunization with fibrinogen results in the generation of anti-citrullinated fibrinogen responses that can also target citrullinated proteins present in tissues other than the synovial joint. This possibility is supported by the reactivity of human RA sera with not only citrullinated proteins generated in inflamed joint tissue but also with citrullinated filaggrin, a protein expressed in stratified epithelium but not in joints. Multiple proteins are citrullinated as part of physiological processes, including formation of the myelin sheath (during which myelin basic protein is citrullinated), cornification of the epidermis (keratin), late-stage differentiation of the epidermis (filaggrin), and modulation of chromatin structure (histones). We postulate that in vitro citrullination of substrate proteins results in their hyper-citrullination and in the generation of many citrulline-containing epitopes that are not representative of the citrulline-containing epitopes formed in vivo; some of these hyper-citrullinated epitopes may be cross-recognized by ACPAs.

The induction of arthritis by immunization with fibrin or with native or in vitro citrullinated fibrinogen has been previously studied. Chronic arthritis was induced in rabbits by systemic immunization with heterologous or autologous fibrin followed by intra-articular injection of fibrin (Dumonde and Glynn. 1962. Br J Exp Pathol 43:373). Immunization of BALB/c mice with native or in vitro citrullinated fibrinogen induced antibodies to citrullinated fibrinogen and CCP but did not evoke arthritis (Hida et al. (2004) J Autoimmun 23:141). Likewise, FIA was not induced in, BALB/c mice in our studies. Rubin and Sonderstrup immunized several mouse strains with in vitro citrullinated human fibrinogen and observed high titers of antibodies against human, but not, mouse, fibrinogen and relatively low titers of anti-citrulline antibodies (Rubin and Sonderstrup (2004) Scand J Immunol 60:112). None of the 600 mice on the various background strains tested (BALB/c, DBA/1, and C57BL/10) developed arthritis. Furthermore, immunization of DBA/1 mice expressing a transgene encoding HLA-DR4*0401 with denatured in vitro citrullinated human fibrinogen induced antibodies against citrullinated fibrinogen but did not evoke arthritis. We also attempted to induce FIA with in vitro citrullinated fibrinogen, and, despite the generation of high-titer anti-CCP antibody responses, no mice developed arthritis. Thus, the induction of arthritis by fibrinogen is restricted both by the degree of fibrinogen citrullination and by genetic susceptibility.

Table 4 summarizes the more commonly used mouse models of RA and compares these models to FIA. The K/B×N spontaneous mouse model of RA begins as a T-cell-dependent response to glucose-6-phosphoisomerase (GPI) and differentiates into an autoantibody-dependent disease involving anti-GPI-IgG (Korganow et. al. (1999) Immunity 10:451). K/B×N mice possess high levels of immune complexes containing GPI but do not develop RF and are weakly positive for anti-CCP antibodies. Matsumoto et al. (2003) Arthritis Rheum 48:944 reported that only 15% of RA patients possess anti-GPI antibodies (12-29% range), and that anti-GPI autoantibodies are also present in other arthritides and are thus not specific for RA. Therefore, GPI does not appear to be a primary autoantigen in human RA.

TABLE 4

Comparison of mouse models of RA.
Table 2: Comparison of mouse models of RA

|  | Dominant Ag | T-cell specificity | B-cell specificity | cell transfer | sera transfer | rheumatoid factor | anti-CCP | Immune complexes | human RA reference |
|---|---|---|---|---|---|---|---|---|---|
| Spontaneous models of RA | | | | | | | | | |
| K/BxN | Rnase TCR Transgenic | glucose-6-phosphate Isomerase (GPI) | GPI | GPI | yes | yes | negative | positive | yes | 15% |
| SKG | ZAP-7D mutation | undefined | undefined | type II collagen | yes | no | positive | positive | yes | none |
| Inducible models of RA | | | | | | | | | |
| CIA | DBA, SJL | type II collagen | type II collagen | type II collagen | no | yes | positive | positive | no | 5-15% |
| FIA | SJL, DBA | fibrinogen (native) | fibrinogen | fibrinogen | yes | yes | positive | positive | yes | 35% |

References: K/BxN (40, 41); SKG (42); CIA (43-50)

The SKG spontaneous mouse model of RA arose from a mutation of the ζ-associated-protein of the 70 kDA (ZAP-70) that results in abnormal thymic T-cell selection and survival of autoreactive clones. Anti-CII autoantibodies are present in sera derived from SKG mice. T cells, thymocytes and bone marrow cells transfer disease, but transfer of SKG serum does not induce arthritis in recipients. Although this model is positive for RF, anti-CCP antibodies, and immune complexes (Table 4), analogous mutations in CD45 and immunologic alterations have not been observed in human RA patients.

In the CIA model CII is used as the immunizing antigen to induce arthritis in rodents. This model is negative for RF, weakly positive for anti-CCP antibodies, and negative for immune complexes (Table 4). Although one group described cell-based adoptive transfer of CIA, most laboratories have not been able to induce arthritis by cell-based adoptive transfer. Transfer of CII specific T cells has been reported in rats, and the only successful transfer in mice has been the induction of microscopic evidence of arthritis by intrasynovial injection of cloned T cell lines. Moreover, the frequency of antibodies reactive to native CII in RA is low (5-15% of RA patients), which suggests that native CII is not a major pathogenic autoantigen in RA. In a cohort of 286 early RA patients, 40% possessed detectable IgG antibodies directed against the citrullinated form of the immunodominant CII epitope C1. Recently, it was shown that anti-citrullinated CII antibodies are pathogenic in a rodent model, suggesting that such responses against citrullinated CII might contribute to arthritis.

In the FIA model described herein, the native form of fibrinogen is used as the immunizing antigen. FIA involves robust T-dell reactivity to native fibrinogen and B-cell reactivity to native fibrinogen, citrullinated fibrinogen, and other candidate RA autoantigens. Disease can be transferred with either fibrinogen-reactive T cells or plasma from FIA mice. Mice with FIA possess RF, anti-CCP antibodies, and IgG immune complexes, all of which are characteristic of a subset of RA patients. Moreover, citrullinated fibrinogen is a prominent target of the autoantibody response in half of anti-CCP+ RA patients. Compared to the arthritis that develops in other murine models of RA, FIA is mild to moderate and therefore more closely resembles human RA. Another advantage of the FIA model is that it does not rely on genetically altered mice expressing a TCR-encoding transgene or mutated form of CD45, but rather uses wild-type SJL or DBA/1 mice, which are common mouse strains that are readily available.

Recent observations have linked the inflammatory and coagulation systems in several autoimmune diseases. Articular inflammation in CIA is accompanied by the upregulation of tissue factor, tissue factor pathway inhibitor, urokinase, and plasminogen activator, suggesting that increased extravascular coagulation may contribute to fibrin deposition within the joint.

Thus, the increased deposition and citrullination of fibrinogen in inflamed joints in human RA could potentiate arthritogenic autoimmune responses against citrullinated fibrinogen. In support of a pathogenic role for components of the coagulation system in inflammatory arthritis, the thrombin inhibitor hirudin was shown to be efficacious in treating CIA. The coagulation cascade has also been implicated in several pathological stages of multiple sclerosis: treatment of experimental autoimmune encephalomyelitis, a Th1-Th17 antigen driven mouse model of multiple sclerosis, with either hirudin or activated protein C (an anticoagulant) ameliorated disease.

In conclusion, we demonstrate that immunization with human fibrinogen containing native citrulline modifications induces an inflammatory arthritis that shares clinical, histological and immunological features with RA. Our results suggest that fibrinogen can be arthritogenic in mice and that FIA is mediated by both autoreactive T-cell and autoantibody responses. Finally, in contrast to the other three mouse models of RA listed in Table 4, we believe FIA is a highly relevant model for the study of human RA because it is based upon autoimmunity against a known autoantigen targeted in approximately half of anti-CCP+ RA patients.

Example 3

Figure 11:
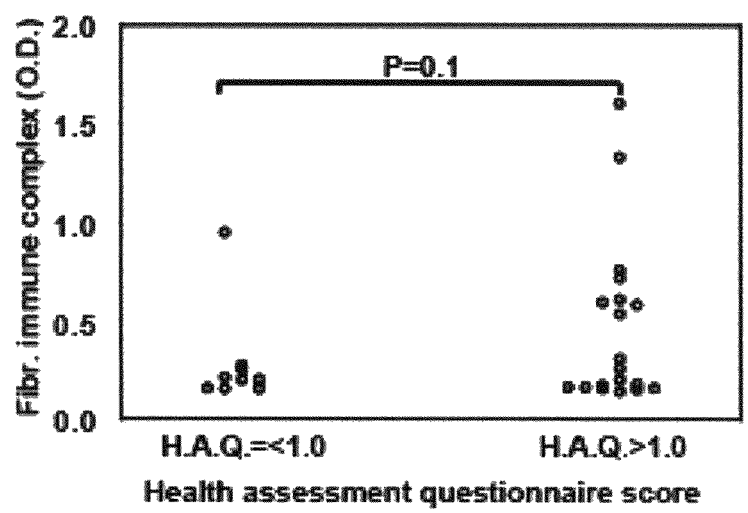
FIG. 11. Higher fibrinogen immune complex correlates with RA patients whose HAQ (Health Assessment Questionaire) score is higher than 1 (indicative of increased disability).
Figure 12:
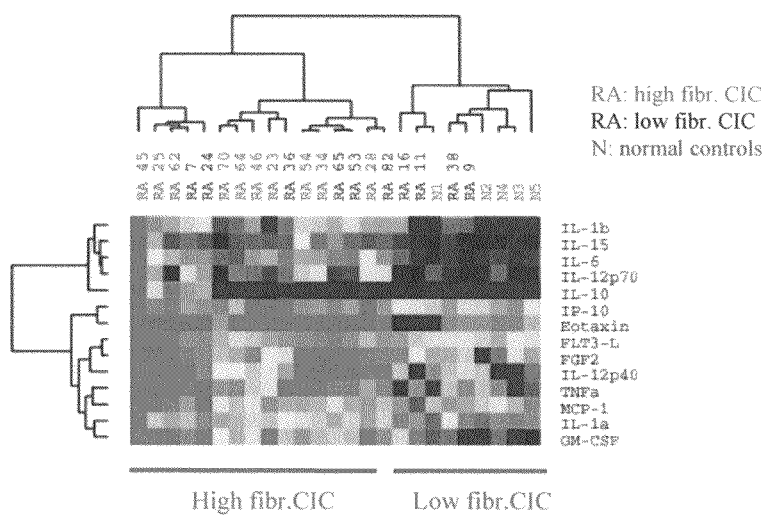
FIG. 12. High fibrinogen immune complex level associates with elevated level of cytokines in RA. Cytokine analysis was done with the human 22-cytokine Beadlyte kit from Upstate and shown as clustered heatmaps.

Molecular Classification of RA Patients to Predict (I) Disease Severity, and (II) Response to Therapy Detection of circulating immune complexes containing fibrinogen and other specific antigens can be used to identify subsets of RA patients with different long-term prognoses and response to therapy. In RA, the presence of circulating immune complexes containing fibrinogen (FIG. 10) predicted more severe disease (FIG. 11) as measured by the Health Assessment Questionaire (HAQ), a measure of disability. Elevated levels of circulating immune complexes containing fibrinogen also correlated with the presence of elevated blood cytokine levels (FIG. 12), and are predictive for more severe disease.

Figure 13:
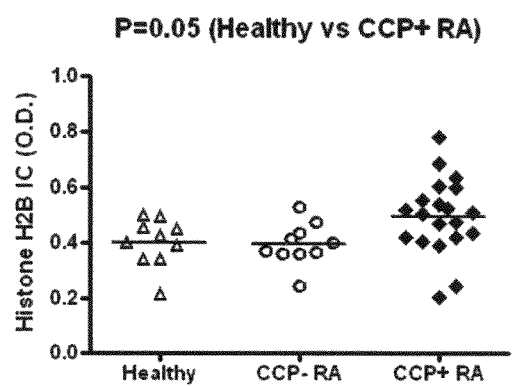
FIG. 13. H2B containing immune complexes are elevated in anti-CCP+ RA plasma. Immune complexes were captured by C1q and H2B containing immune complexes were detected by anti-H2B antibody.
Figure 14:
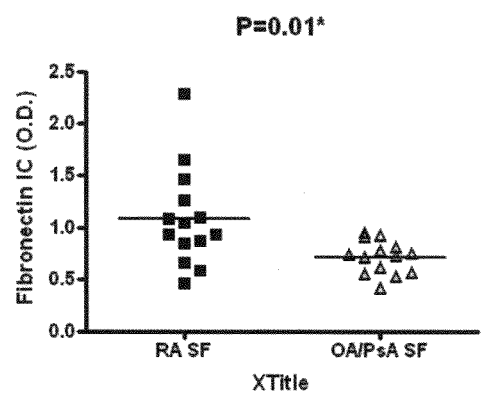
FIG. 14. Fibronectin containing immune complexes were demonstrated in RA synovial fluid. C1q was used to coat the plates. Synovial fluid from different patients were diluted 1:10 for immune complex capture. Fibronectin containing immune complexes were detected with an anti-fibronectin antibody.
Figure 15:
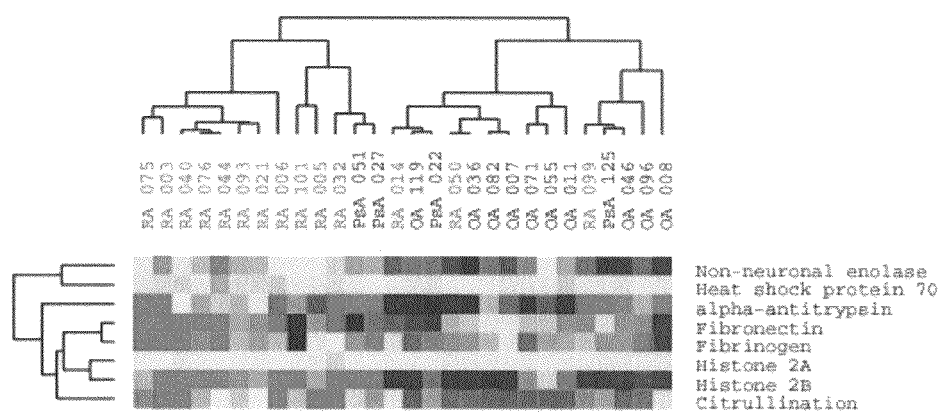
FIG. 15. Different immune complexes existing in RA synovial fluid. C1q was used to coat the plates. Synovial fluid from different patients were diluted 1:10 for immune complex capture. Different immune complexes were detected with anti-non-neuronal enolase, anti-heat shock protein 70, anti-alpha-1-antitrypsin, anti-fibronectin, anti-fibrinogen, anti-histone 2A and 2B, and anti-modified citrulline antibodies.

Circulating immune complexes containing histone 2B (H2B) (FIG. 13), fibronectin (FIG. 14) and other antigens (FIG. 15) are also detected in RA patient blood, and are detected using secondary antibodies specific for these other antigens (after capturing the circulating immune complexes with C1q protein or anti-C1q antibody). Bioinformatics algorithms are applied to identify associations of circulating immune complexes for predicting disease severity in RA, based on HAQ scores, DAS (Disease Activity Scores), Sharp scores (a measure of bone erosions) and other clinical outcome parameters. Bioinformatics algorithms are also applied to identify associations of circulating immune complexes for predicting response to particular therapeutic against, including anti-TNF drugs, CTLA4-Ig, rituximab and anti-IL-6 therapy. Bioinformatics algorithms are also applied to identify combinations of biomarkers including circulating immune complexes, blood autoantibodies and/or blood cytokines that have increased predictive value for the severity of disease or likelihood to response to a particular therapeutic agent.

What is claimed is:

1. A method for the prognosis of the severity of rheumatoid arthritis in a human individual, the method comprising:

denoting circulating immune complexes containing citrullinated fibrinogen and immunoglobulin in a sample of blood or derivative therefrom obtained from the individual;

analyzing the fibrinogen immune complex content in said sample relative to a normal control by contacting the blood sample with C1q protein;

contacting immune complexes bound to the C1q protein with an agent that selectively binds to fibrinogen;

detecting the presence of a fibrinogen containing immune complexes;

wherein the presence of said fibrinogen containing immune complexes, compared to a control sample, is indicative of positive binding; and providing an assessment of prognosis for said individual, where the presence of the immune complexes containing fibrinogen is indicative of a more severe disease prognosis.

2. The method of claim 1, wherein said agent selectively binds to fibrinogen is an antibody that specifically recognizes human fibrinogen.

3. The method of claim 1, wherein said immune complexes containing fibrinogen is predictive for response to a specific treatment, such as anti-TNF antibodies, CTLA4-Ig, rituximab, or anti-IL-6 antibodies.

4. The method of claim 1, wherein the human individual is a juvenile human, and the presence of the immune complexes containing fibrinogen is indicative of a disease phenotype associated with adult rheumatoid arthritis.

* * * * *